(12) United States Patent
Iadonato et al.

(10) Patent No.: US 9,878,058 B2
(45) Date of Patent: *Jan. 30, 2018

(54) SHK-BASED PHARMACEUTICAL COMPOSITIONS AND METHODS OF MANUFACTURING AND USING THE SAME

(71) Applicant: Kineta One, LLC, Seattle, WA (US)

(72) Inventors: Shawn P. Iadonato, Seattle, WA (US); Eric J. Tarcha, Seattle, WA (US)

(73) Assignee: Kv1.3 Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/836,700

(22) Filed: Aug. 26, 2015

(65) Prior Publication Data

US 2016/0045627 A1 Feb. 18, 2016

Related U.S. Application Data

(62) Division of application No. 14/124,669, filed as application No. PCT/US2012/040857 on Jun. 5, 2012, now Pat. No. 9,381,261.

(60) Provisional application No. 61/625,578, filed on Apr. 17, 2012, provisional application No. 61/493,868, filed on Jun. 6, 2011.

(51) Int. Cl.
| | | |
|---|---|---|
| *A61K 38/16* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 49/00* | (2006.01) |
| *C07K 14/00* | (2006.01) |
| *A61K 38/17* | (2006.01) |
| *C07K 14/435* | (2006.01) |
| *A61K 51/08* | (2006.01) |
| *A61K 51/04* | (2006.01) |
| *B01L 3/12* | (2006.01) |
| *B01L 9/00* | (2006.01) |
| *B01L 99/00* | (2010.01) |

(52) U.S. Cl.
CPC .......... *A61K 49/0004* (2013.01); *A61K 38/16* (2013.01); *A61K 38/1767* (2013.01); *A61K 49/0002* (2013.01); *A61K 51/0482* (2013.01); *A61K 51/088* (2013.01); *C07K 14/00* (2013.01); *C07K 14/43504* (2013.01); *A61K 38/00* (2013.01); *B01L 3/12* (2013.01); *B01L 9/00* (2013.01); *B01L 99/00* (2013.01)

(58) Field of Classification Search
None
See application file for complete search history.

(56) References Cited

U.S. PATENT DOCUMENTS

| | | |
|---|---|---|
| 4,352,883 A | 10/1982 | Lim |
| 4,353,888 A | 10/1982 | Sefton |
| 4,883,666 A | 11/1989 | Sabel et al. |
| 4,968,733 A | 11/1990 | Muller et al. |
| 4,976,859 A | 12/1990 | Wechs |
| 5,084,350 A | 1/1992 | Chang et al. |
| 5,158,881 A | 10/1992 | Aebischer et al. |
| 5,284,761 A | 2/1994 | Aebischer et al. |
| 5,791,466 A | 8/1998 | Tsals |
| 6,077,680 A | 6/2000 | Kern et al. |
| 7,833,979 B2 | 11/2010 | Sullivan et al. |
| 7,918,824 B2 | 4/2011 | Bishop et al. |
| 8,080,523 B2 | 12/2011 | Beeton et al. |
| 8,440,621 B2 | 5/2013 | Chandy et al. |
| 9,381,261 B2 * | 7/2016 | Iadonato ............ A61K 38/1767 |
| 2008/0221024 A1 | 9/2008 | Chandy et al. |
| 2009/0263462 A1 | 10/2009 | King |
| 2011/0163469 A1 | 7/2011 | Little et al. |
| 2014/0221271 A1 | 8/2014 | Iadonato et al. |
| 2015/0072940 A1 | 3/2015 | Chandy et al. |
| 2016/0338967 A1* | 11/2016 | Iadonato ............... A61K 9/0019 |

FOREIGN PATENT DOCUMENTS

| | | |
|---|---|---|
| CN | 101072577 A | 11/2007 |
| WO | WO9219195 A1 | 11/1992 |
| WO | WO9505452 A2 | 2/1995 |
| WO | WO199823639 A2 | 6/1998 |
| WO | WO1999013895 A1 | 3/1999 |

(Continued)

OTHER PUBLICATIONS

Altschul, et al.,"Basic Local Alignment Search Tool", J. Mol. Biol., vol. 215, 1990, pp. 403-410.
Arano, et al., "Reassessment of Diethylenetriaminepentaacetic Acid (DTPA) as a Chelating Agent for Indium-111 Labeling of Polypeptides Using a Newly Synthesized Monoreactive DTPA Derivative", J. Med. Chem., 1996, vol. 39, No. 18, pp. 3451-3460.
Bastin, et al.,"Salt Selection and Optimisation Procedures for Pharmaceutical New Chemical Entities", Org. Process Res. Dev., vol. 4, No. 5, 2000, pp. 427-435.

(Continued)

*Primary Examiner* — Hasan Ahmed
*Assistant Examiner* — Thea D'Ambrosio
(74) *Attorney, Agent, or Firm* — Christensen O'Connor Johnson Kindness PLLC

(57) ABSTRACT

Disclosed herein are pharmaceutical compositions having the sequence Arg-Ser-Cys-Ile-Asp-Thr-Ile-Pro-Lys-Ser-Arg-Cys-Thr-Ala-Phe-Gln-Cys-Lys-His-Ser-Xaa-Lys-Tyr-Arg-Leu-Ser-Phe-Cys-Arg-Lys-Thr-Cys-Gly-Thr-Cys (SEQ ID NO:1). The disclosed compositions can include an acid or amide at the C-terminus of SEQ ID NO: 1 and the polypeptide can be attached to an organic or inorganic chemical entity that has an anionic charge. The polypeptide can be detectably labeled for diagnostic purposes. Methods of manufacturing and using the pharmaceutical compounds are also disclosed.

6 Claims, 7 Drawing Sheets

(56) References Cited

FOREIGN PATENT DOCUMENTS

| WO | WO2009021289 A1 | 2/2009 |
|----|-----------------|--------|
| WO | WO2010108154 A2 | 9/2010 |

OTHER PUBLICATIONS

Beeton, et al.,"Targeting Effector Memory T Cells with a Selective Peptide Inhibitor of Kv1.3 Channels for Therapy of Autoimmune Diseases", Mol. Pharmacol., vol. 67, No. 4, 2005, pp. 1369-1381.
Bodei, et al.,"Receptor-Mediated Radionuclide Therapy with 90Y-DOTATOC in Association with Amino Acid Infusion: A Phase I Study", Eur. J. Nucl. Med., vol. 30, 2003, pp. 207-216.
Burke, et al.,"Phosphotyrosyl Mimetics in the Development of Signal Transduction Inhibitors", Acc. Chem. Res., vol. 36, No. 6, 2003, pp. 426-433.
Castaneda, et al.,"Characterization of a Potassium Channel Toxin from the Caribbean Sea Anemone Stichodactyla helianthus", Toxicon, vol. 33, No. 5, 1995, pp. 603-613.
Chi, et al.,"Development of a Sea Anemone Toxin as an Immunomodulator for Therapy of Autoimmune Diseases", Toxicon, vol. 59, No. 4, 2012, pp. 529-546.
de Jong, et al.,"Megalin Is Essential for Renal Proximal Tubule Reabsorption of 111In-DTPA-Octreotide", J. Nucl. Med., vol. 46, No. 10, 2005, pp. 1696-1700.
Gotthardt, et al.,"Indication for Different Mechanisms of Kidney Uptake of Radiolabeled Peptides", J. Nuc. Med., vol. 48, No. 4, 2007, pp. 596-601.
Goules, et al.,"Elevated Levels of Soluble CD40 Ligand (sCD4OL) in Serum of Patients with Systemic Autoimmune Diseases", J. Autoimmun., vol. 26, 2006, pp. 165-171.
Hasegawa, et al.,"Isolation and cDNA Cloning of a Potassium Channel Peptide Toxin from the Sea Anemone Anemonia erythraea", Toxicon, vol. 48, 2006, pp. 536-542.
Jaravine, et al.,"Three-Dimensional Structure of Toxin OSK1 from Orthochirus scrobiculosus Scorpion Venom", Biochemistry, vol. 36, No. 6, 1997, pp. 1223-1232.
Kaiser, et al., "Color Test for Detection of Free Terminal Amino Groups in the Solid-Phase Synthesis of Peptides", Anal. Biochem., vol. 34, No. 2, 1970, pp. 595-598.
Kalman, et al.,"ShK-Dap22, a Potent Kv1.3-specific Immunosuppressive Polypeptide", J. Biol. Chem., vol. 273, No. 49, 1998, pp. 32697-32707.
Kapoor, "Recent Trends in the Synthesis of Linear Peptides", J. Pharm. Sci., vol. 59, No. 1, 1970, pp. 1-27.
Liu, et al.,"IL-15 is Highly Expressed in Inflammatory Bowel Disease and Regulates Local T Cell-Dependent Cytokine Production", J. Immunol., vol. 164, No. 7, 2000, pp. 3608-3615.
McCloskey, et al.,"Kv1.3 is the Exclusive Voltage-Gated K+ Channel of Platelets and Megakaryocytes: Roles in Membrane Potential, Ca2+ Signalling and Platelet Count", J. Physiol., vol. 588, Part 9, 2010, pp. 1399-1406.
NCBI Database, GenBank Accession No. P29187, 2 pages, 1993.
Nicolas, et al.,"A Study of the Use of NH41 for the Reduction of Methionine Sulfoxide in Peptides Containing Cysteine and Cystine", Tetrahedron, vol. 51, No. 19, 1995, pp. 5701-5710.
Office Action Dated Feb. 13, 2014 in Taiwan Application No. 101120237.
Office Action dated Mar. 27, 2015 in U.S. Appl. No. 14/124,669.
Office Action dated Dec. 19, 2014 in Singapore Application No. 2013089842.
Office Action dated Sep. 26, 2014 in Taiwan Application No. 101120237.
Office Action dated Sep. 29, 2014 in Chinese Application No. 201280035051.7.
Orcutt, et al., "Engineering an Antibody with Picomolar Affinity to DOTA Chelates of Multiple Radionuclides for Pretargeted Radioimmunotherapy and Imaging", Nucl. Med. Biol., vol. 38, 2010, pp. 223-233.
Pennington, et al., "An Essential Binding Surface for ShK Toxin Interaction with Rat Brain Potassium Channels", Biochemistry, vol. 35, No. 51, 1996, pp. 16407-16411.
Pennington, et al.,"Chemical Synthesis and Characterization of ShK Toxin: A Potent Potassium Channel Inhibitor from a Sea Anemone", Int. J. Pept. Prot. Res., vol. 46., No. 5, 1995, pp. 354-358.
Pennington, et al.,"Engineering a Stable and Selective Peptide Blocker of the Kv1.3 Channel in T-Lymphocytes", Mol. Pharmacol., vol. 75, No. 4, 2009, pp. 762-773.
Pennington, et al.,"Identification of Three Separate Binding Sites on SHK Toxin, a Potent Inhibitor of Voltage-Dependent Potassium Channels in Human T-Lymphocytes and Rat Brain", Biochem. Biophys. Res. Commun., vol. 219, No. 3, 1996, pp. 696-701.
Rivier, et al. "Solid-Phase Synthesis of Somatostatin and Glucagon-Selective Analogs in Gram Quantities", Biopolymers, vol. 17, No. 8, 1978, pp. 1927-1938.
Roberts, et al.,"Chemistry for Peptide and Protein PEGylation", Adv. Drug Deliv. Rev., vol. 54, No. 4, 2002, pp. 459-476.
Schultz, et al., "Synthesis of a DOTA-Biotin Conjugate for Radionuclide Chelation via Cu-Free Click Chemistry," Org. Lett., vol. 12, 2010, pp. 2398-2401.
Sosabowski, et al.,"Conjugation of DOTA-Like Chelating Agents to Peptides and Radiolabeling with Trivalent Metallic Isotopes", Nat. Protoc., vol. 1, No. 2, 2006, pp. 972-976.
Search Report and Written Opinion dated Jan. 25, 2013 in International Application No. PCT/US2012/040857.
Search Report and Written Opinion dated Jan. 30, 2015 in International Application No. PCT/US2014/047691.
Search Report dated Apr. 29, 2015 in European Application No. 12797181.0.
Search Report and Written Opinion dated Jun. 25, 2015 in International Application No. PCT/US2014/072253.
Declaration of Non-Establishment of Search Report and Written Opinion dated Jun. 27, 2014 in International Application No. PCT/US2014/020771.
Suh, et al.,"A Survey of Putative Secreted and Transmembrane Proteins Encoded in the C. elegans Genome", BMC Genomics, vol. 13, 2012, pp. 1-18.
Trowbridge, et al.,"The Origin of Platelet Count and Volume", Clin. Phys. Physiol. Meas., vol. 5, No. 3, 1984, pp. 145-170.
Tudor, et al. "Ionisation Behaviour and Solution Properties of the Potassium-Channel Blocker ShK Toxin", Eur. J. Biochem., vol. 251, 1998, pp. 133-141.
Upadhyay, et al., "Anti-Obesity Effect of Shk-186, a K+ Channel Blocker", Faseb Journal, 2010, vol. 24, Abstract, Conference on Experimental Biology, Anaheim, CA.
Wulff, et al.,"Design of a Potent and Selective Inhibitor of the Intermediate-Conductance Ca2+-activated K+ Channel, IKCa1: A Potential Immunosuppressant", PNAS, vol. 97, No. 14, 2000, pp. 8151-8156.
Wulff, et al.,"The Voltage-Gated Kv1.3 K+ Channel in Effector Memory T Cells as New Target for MS", J. Clin. Invest., vol. 111, 2003, pp. 1703-1713.
Yamaguchi, et al., "Screening and cDNA Cloning of Kv1 Potassium Channel Toxins in Sea Anemones", Mar. Drugs vol. 8, No. 12, 2010, pp. 2893-2905.
Furman, et al., "Early Engineering Approaches to Improve Peptide Developability and Manufacturability", AAPS Journal, 2015, vol. 17 (1), pp. 111-120.
Office Action dated Nov. 6, 2015 in U.S. Appl. No. 14/124,669.
Office Action dated Jul. 21, 2015 in Singapore Application No. 201308984-2.
Witt, et al., "Peptide Drug Modifications to Enhance Bioavailability and Blood-Brain Barrier Permeability", Peptides, 2001, vol. 22 (12), pp. 2329-2343.

* cited by examiner

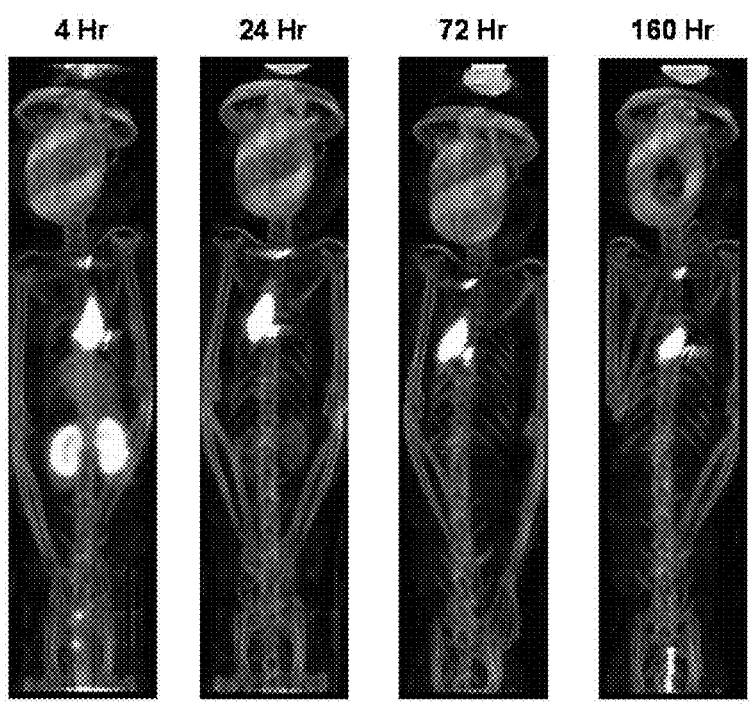
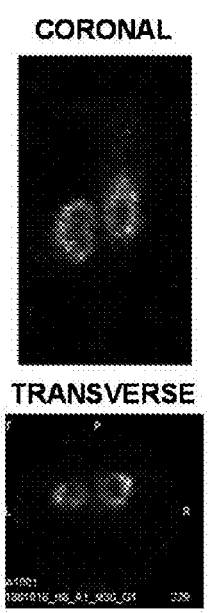
FIG. 1A
FIG. 1B

```
                        SEQUENCE LISTING

<160> NUMBER OF SEQ ID NOS: 8

<210> SEQ ID NO 1
<211> LENGTH: 35
<212> TYPE: PRT
<213> ORGANISM: Artificial Sequence
<220> FEATURE:
<223> OTHER INFORMATION: ShK Polypeptide
<220> FEATURE:
<221> NAME/KEY: VARIANT
<222> LOCATION: (21)..(21)
<223> OTHER INFORMATION: Xaa is Met or Nle

<400> SEQUENCE: 1

Arg Ser Cys Ile Asp Thr Ile Pro Lys Ser Arg Cys Thr Ala Phe Gln
1               5                   10                  15

Cys Lys His Ser Xaa Lys Tyr Arg Leu Ser Phe Cys Arg Lys Thr Cys
            20                  25                  30

Gly Thr Cys
        35

<210> SEQ ID NO 2
<211> LENGTH: 37
<212> TYPE: PRT
<213> ORGANISM: Artificial Sequence
<220> FEATURE:
<223> OTHER INFORMATION: ShK Polypeptide - ShK-186
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MISC_FEATURE
<222> LOCATION: (2)..(2)
<223> OTHER INFORMATION: Xaa is aminoethyloxyethyloxy-acetyl linker
<220> FEATURE:
<221> NAME/KEY: MOD_RES
<222> LOCATION: (37)..(37)
<223> OTHER INFORMATION: AMIDATION

<400> SEQUENCE: 2

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 3
<211> LENGTH: 35
<212> TYPE: PRT
<213> ORGANISM: Artificial Sequence
<220> FEATURE:
<223> OTHER INFORMATION: ShK Polypeptide
<220> FEATURE:
<221> NAME/KEY: MOD_RES
<222> LOCATION: (35)..(35)
<223> OTHER INFORMATION: AMIDATION

<400> SEQUENCE: 3

Arg Ser Cys Ile Asp Thr Ile Pro Lys Ser Arg Cys Thr Ala Phe Gln
1               5                   10                  15
```

```
Cys Lys His Ser Met Lys Tyr Arg Leu Ser Phe Cys Arg Lys Thr Cys
            20                  25                  30

Gly Thr Cys
        35
```

<210> SEQ ID NO 4
<211> LENGTH: 37
<212> TYPE: PRT
<213> ORGANISM: Artificial Sequence
<220> FEATURE:
<223> OTHER INFORMATION: ShK Polypeptide - ShK-192
<220> FEATURE:
<221> NAME/KEY: MISC_FEATURE
<222> LOCATION: (1)..(1)
<223> OTHER INFORMATION: Xaa is 4-phosphono-L-phenylalanine
<220> FEATURE:
<221> NAME/KEY: MISC_FEATURE
<222> LOCATION: (2)..(2)
<223> OTHER INFORMATION: Xaa is an 2-[2-(2-aminoethoxy)ethoxy]acetyl
      linker
<220> FEATURE:
<221> NAME/KEY: DISULFID
<222> LOCATION: (5)..(37)
<220> FEATURE:
<221> NAME/KEY: DISULFID
<222> LOCATION: (14)..(30)
<220> FEATURE:
<221> NAME/KEY: DISULFID
<222> LOCATION: (19)..(34)
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (37)..(37)
<223> OTHER INFORMATION: AMIDATION

<400> SEQUENCE: 4

```
Xaa Xaa Arg Ser Cys Ile Asp Thr Ile Pro Lys Ser Arg Cys Thr Ala
1               5                   10                  15

Phe Gln Cys Lys His Ser Xaa Lys Tyr Arg Leu Ser Phe Cys Arg Lys
            20                  25                  30

Thr Cys Gly Thr Cys
            35
```

<210> SEQ ID NO 5
<211> LENGTH: 37
<212> TYPE: PRT
<213> ORGANISM: Artificial Sequence
<220> FEATURE:
<223> OTHER INFORMATION: ShK Polypeptide - ShK-198
<220> FEATURE:
<221> NAME/KEY: MISC_FEATURE
<222> LOCATION: (2)..(2)
<223> OTHER INFORMATION: Xaa is an aminoethyloxyethyloxy-acetyl linker
<220> FEATURE:
<221> NAME/KEY: MOD_RES
<222> LOCATION: (37)..(37)
<223> OTHER INFORMATION: AMIDATION

<400> SEQUENCE: 5

```
Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
            35
```

```
<210> SEQ ID NO 6
<211> LENGTH: 39
<212> TYPE: PRT
<213> ORGANISM: Artificial Sequence
<220> FEATURE:
<223> OTHER INFORMATION: ShK Polypeptide - ShK-221
<220> FEATURE:
<221> NAME/KEY: MISC_FEATURE
<222> LOCATION: (1)..(1)
<223> OTHER INFORMATION: Xaa is 1,4,7,10-tetraazacyclododecane-1,4,7,10-
      tetraacetic acid
<220> FEATURE:
<221> NAME/KEY: MISC_FEATURE
<222> LOCATION: (2)..(2)
<223> OTHER INFORMATION: Xaa is aminohexanoic acid
<220> FEATURE:
<221> NAME/KEY: MISC_FEATURE
<222> LOCATION: (4)..(4)
<223> OTHER INFORMATION: Xaa is an aminoethyloxyethyloxy-acetyl linker
<220> FEATURE:
<221> NAME/KEY: MOD_RES
<222> LOCATION: (39)..(39)
<223> OTHER INFORMATION: AMIDATION

<400> SEQUENCE: 6

Xaa Xaa Tyr Xaa Arg Ser Cys Ile Asp Thr Ile Pro Lys Ser Arg Cys
1               5                   10                  15

Thr Ala Phe Gln Cys Lys His Ser Met Lys Tyr Arg Leu Ser Phe Cys
            20                  25                  30

Arg Lys Thr Cys Gly Thr Cys
        35

<210> SEQ ID NO 7
<211> LENGTH: 35
<212> TYPE: PRT
<213> ORGANISM: Artificial Sequence
<220> FEATURE:
<223> OTHER INFORMATION: ShK Polypeptide
<220> FEATURE:
<221> NAME/KEY: VARIANT
<222> LOCATION: (21)..(21)
<223> OTHER INFORMATION: Xaa is Met or Ile

<400> SEQUENCE: 7

Arg Ser Cys Ile Asp Thr Ile Pro Lys Ser Arg Cys Thr Ala Phe Gln
1               5                   10                  15

Cys Lys His Ser Xaa Lys Tyr Arg Leu Ser Phe Cys Arg Lys Thr Cys
            20                  25                  30

Gly Thr Cys
        35

<210> SEQ ID NO 8
<211> LENGTH: 38
<212> TYPE: PRT
<213> ORGANISM: Artificial Sequence
<220> FEATURE:
<223> OTHER INFORMATION: ShK Polypeptide
<220> FEATURE:
<221> NAME/KEY: MISC_FEATURE
<222> LOCATION: (1)..(1)
<223> OTHER INFORMATION: Xaa is p-phosphatityl-phenylalanine
<220> FEATURE:
<221> NAME/KEY: MISC_FEATURE
<222> LOCATION: (3)..(3)
<223> OTHER INFORMATION: Xaa is an aminoethyloxyethyloxy-acetyl linker
<220> FEATURE:
<221> NAME/KEY: MOD_RES
<222> LOCATION: (38)..(38)
<223> OTHER INFORMATION: AMIDATION

<400> SEQUENCE: 8
```

```
Xaa Phe Xaa Arg Ser Cys Ile Asp Thr Ile Pro Lys Ser Arg Cys Thr
1               5                   10                  15

Ala Phe Gln Cys Lys His Ser Met Lys Tyr Arg Leu Ser Phe Cys Arg
            20              25                  30

Lys Thr Cys Gly Thr Cys
        35
```

SHK-BASED PHARMACEUTICAL COMPOSITIONS AND METHODS OF MANUFACTURING AND USING THE SAME

CROSS-REFERENCE TO RELATED APPLICATIONS

This application is a divisional of U.S. application Ser. No. 14/124,669, filed on Dec. 6, 2013, which is a U.S. national phase application based on International Application No. PCT/US2012/040857, filed on Jun. 5, 2012, which claims priority to U.S. Provisional Application No. 61/493,868 filed on Jun. 6, 2011 and U.S. Provisional Application No. 61/625,578 filed on Apr. 17, 2012, all of which are incorporated by reference in their entirety herein.

STATEMENT OF GOVERNMENT INTEREST

The United States government has rights in the present disclosure pursuant to National Institutes of Health National Institute of Allergy and Infectious Diseases Grants R43AI085691 and NIH R01NS48252.

FIELD OF THE DISCLOSURE

The compositions and methods disclosed herein relate generally to the use of ShK-based pharmaceutical compositions to treat, prevent and/or alleviate symptoms associated with diseases and disorders in which memory T cells play a role, including autoimmune diseases and metabolic disorders.

SUMMARY OF THE DISCLOSURE

Many immune-related human diseases and metabolic disorders are attributed to the action of memory T cells. Such immune-related diseases include, among others, autoimmune diseases such as multiple sclerosis, type-1 diabetes mellitus, rheumatoid arthritis, and psoriasis. Examples of metabolic disorders include obesity, Type 2 diabetes, hypercholesterolemia, coronary artery disease, metabolic syndrome, metabolic syndrome X, insulin resistance, hyperlipidemia, lipodystrophy, dyslipidemia, hypertriglyceridemia, glucose intolerance and hypertension.

Two categories of memory T cells are known: central memory T cells ($T_{CM}$) and effector memory T cells ($T_{EM}$). Upon activation, $T_{EM}$ cells up-regulate Kv1.3 $K^+$ ion channels. The antigen-driven proliferation of TEM cells is sensitive to Kv1.3 $K^+$ ion channels blockers (Wulff et al., J. Clin. Invest. 111:1703-1713, 2003), and the polypeptide ShK, originally isolated from the Caribbean sea anemone *Stichodactyla helianthus*, serves as such a blocker. By blocking Kv1.3 channels, ShK suppresses proliferation of TEM cells at picomolar concentrations.

One embodiment disclosed herein includes a pharmaceutical composition comprising an ShK polypeptide having the sequence Arg-Ser-Cys-Ile-Asp-Thr-Ile-Pro-Lys-Ser-Arg-Cys-Thr-Ala-Phe-Gln-Cys-Lys-His-Ser-Xaa-Lys-Tyr-Arg-Leu-Ser-Phe-Cys-Arg-Lys-Thr-Cys-Gly-Thr-Cys (SEQ ID NO:1; wherein Xaa is Met or Nle).

Another embodiment includes a pharmaceutical composition comprising an ShK polypeptide having the formula Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (SEQ ID NO:3).

Another embodiment includes a pharmaceutical composition comprising an ShK polypeptide having the formula p-phospho-Tyr-AEEA-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (ShK-186; SEQ ID NO:2).

Another embodiment includes a pharmaceutical composition comprising an ShK polypeptide having the formula L-Cysteinamide, 4-phosphono-L-phenylalanyl-2-[2-(2-aminoethoxy)ethoxy]acetyl-L-arginyl-L-seryl-L-cysteinyl-L-isoleucyl-L-α-aspartyl-L-threonyl-L-isoleucyl-L-prolyl-L-lysyl-L-seryl-L-arginyl-L-cysteinyl-L-threohyl-L-alanyl-L-phenylalanyl-L-glutaminyl-L-cysteinyl-L-Lysyl-L-histidyl-L-seryl-L-norleucyl-L-lysyl-L-tyrosyl-L-arginyl-L-leucyl-L-seryl-L-phenylalanyl-L-cysteinyl-L-arginyl-L-lysyl-L-threonyl-L-cysteinylglycyl-L-threonyl-, cyclic (5→37),(14→30),(19→34)-tris(disulfide) (referred to herein as ShK-192, CAS Registry Number 1159528-26-3; SEQ ID NO:4), wherein the ShK-192 polypeptide is attached to an organic or inorganic chemical entity that has an anionic charge, and the C-terminus is an acid or an amide.

Another embodiment includes a pharmaceutical composition comprising an ShK polypeptide having the formula Tyr-AEEA-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (ShK-198; SEQ ID NO:5).

In another embodiment, ShK polypeptides are attached to an organic or inorganic chemical entity that has an anionic charge. In another embodiment, the C-terminus is an acid or an amide. In another embodiment the ShK polypeptides are attached to an organic or inorganic chemical entity that has an anionic charge and the C-terminus is an acid or an amide.

In another embodiment, one or more chemical entities are attached to the N terminus of the ShK polypeptide. In another embodiment, the chemical entity can be attached to the N-terminus of the ShK polypeptide through a linking molecule or linking group. In another embodiment, the chemical entity is attached to the N-terminus of the ShK polypeptide by an aminoethyloxyethyloxy-acetyl linker.

In another embodiment, chemical entities are selected from the group consisting of L-Pmp(OH$_2$); D-Pmp(OH$_2$); D-Pmp(OHEt); L-Pmp(Et$_2$); D-Pmp(Et$_2$); L-Tyr; L-Tyr (PO$_3$H$_2$); L-Phe(p-NH$_2$); L-Phe(p-CO$_2$H); L-Aspartate; D-Aspartate; L-Glutamate; and D-Glutamate.

In another embodiment, chemical entity/linker combinations are selected from the group consisting of AEEAc-L-Pmp(OH$_2$); AEEAc-D-Pmp(OH$_2$); AEEAc-D-Pmp(OHEt); AEEAc-L-Pmp(Et$_2$); AEEAc-D-Pmp(Et$_2$); AEEAc-L-Tyr; AEEAc-L-Tyr(PO$_3$H$_2$); AEEAc-L-Phe(p-NH$_2$); AEEAc-L-Phe(p-CO$_2$H); AEEAc-L-Aspartate; AEEAc-D-Aspartate; AEEAc-L-Glutamate; and AEEAc-D-Glutamate.

In another embodiment, the ShK polypeptide is provided within the pharmaceutical composition as a pharmaceutically acceptable salt thereof. In another embodiment, the pharmaceutically acceptable salt is an acetate. In another embodiment, the pharmaceutically acceptable salt is potassium acetate or sodium acetate.

In another embodiment, the pharmaceutical composition is provided in an aqueous carrier.

In another embodiment, the pH of the pharmaceutical composition is between 5 and 7. In another embodiment, the pH of the pharmaceutical composition is 6.0.

In another embodiment, the pharmaceutical composition further comprises a surfactant in an amount effective to dissolve the ShK polypeptide in an aqueous carrier. In another embodiment, the surfactant is polysorbate 20. In another embodiment, the surfactant is polysorbate 20 at 0.05 w/v %.

In another embodiment, the pharmaceutical composition further comprises 10 mM sodium phosphate. In another embodiment, the pharmaceutical composition further comprises 150 mM NaCl.

In another embodiment, the ShK polypeptide is present at an amount from 0.01 mg/ml to 500 mg/ml. In additional embodiments, the ShK polypeptide can be provided in amount of 0.01, 0.1, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 150, 200, 250, 300, 350, 400, 450 or 500 mg/ml.

In another embodiment, the ShK polypeptide is obtained from a natural source. In another embodiment, the ShK polypeptide is synthetic. In another embodiment the ShK polypeptides include a mixture of natural and synthetic ShK polypeptides.

Embodiments described herein also include lyophilized pharmaceutical compositions produced beginning with a composition described herein. In one embodiment, the lyophilized pharmaceutical composition comprises 8-12% acetate content by weight. In another embodiment, the lyophilized pharmaceutical composition comprises 10-11% acetate content by weight.

In another embodiment of the lyophilized pharmaceutical compositions, the water content of the pharmaceutical composition is less than 5%. In another embodiment of the lyophilized pharmaceutical compositions, the water content is less than 4.0%. In another embodiment of the lyophilized pharmaceutical compositions, the water content is less than 3.5%.

In another embodiment the pharmaceutical compositions are provided in a packaging material. In another embodiment, the pharmaceutical compositions are formulated for long-term storage. In another embodiment, the pharmaceutical compositions are contained in a sterile glass vial and instructed to be stored at −70° C.

In another embodiment, the pharmaceutical compositions are formulated for subcutaneous administration. In another embodiment, the pharmaceutical compositions are contained in a sterile syringe.

One embodiment includes a pharmaceutical composition comprising a pharmaceutically acceptable salt of an ShK polypeptide having the sequence Arg-Ser-Cys-Ile-Asp-Thr-Ile-Pro-Lys-Ser-Arg-Cys-Thr-Ala-Phe-Gln-Cys-Lys-His-Ser-Xaa-Lys-Tyr-Arg-Leu-Ser-Phe-Cys-Arg-Lys-Thr-Cys-Gly-Thr-Cys (SEQ ID NO:1; wherein Xaa is Met or Nle); 10 mM sodium phosphate; 150 mM NaCl; and Polysorbate 20 at 0.05 w/v %, wherein the ShK polypeptide is attached to an organic or inorganic chemical entity that has an anionic charge, the C-terminus is an acid or an amide and the composition has a pH of 6.0.

Another embodiment includes a pharmaceutical composition comprising a pharmaceutically acceptable salt of an ShK polypeptide having the formula Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (SEQ ID NO:3); 10 mM sodium phosphate; 150 mM NaCl; and Polysorbate 20 at 0.05 w/v %, wherein the ShK polypeptide is attached to an organic or inorganic chemical entity that has an anionic charge and the composition has a pH of 6.0.

Another embodiment includes a pharmaceutical composition comprising a pharmaceutically acceptable salt of an ShK polypeptide having the formula p-phospho-Tyr-AEEA-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (ShK-186; SEQ ID NO:2); 10 mM sodium phosphate; 150 mM NaCl; and Polysorbate 20 at 0.05 w/v % and wherein the composition has a pH of 6.0.

Another embodiment includes a pharmaceutical composition comprising an ShK polypeptide having the formula Tyr-AEEA-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$ (ShK-198; SEQ ID NO:5); 10 mM sodium phosphate; 150 mM NaCl; and Polysorbate 20 at 0.05 w/v % and wherein the composition has a pH of 6.0.

Embodiments disclosed herein also include units of manufacture for pharmaceutical use. One embodiment of such a unit of manufacture comprises at least one glass vial prepared under sterile conditions that contains a pharmaceutical composition described herein. In another embodiment, the pharmaceutical composition within the glass vial is stable for at least six months at −70° C. In another embodiment, the unit of manufacture further comprises instructions for diluting and preparing the pharmaceutical composition for administration to a human.

In another embodiment, the unit of manufacture for pharmaceutical use comprises at least one sterile syringe containing a pharmaceutical composition described herein. In another embodiment, the unit of manufacture further comprises instructions for administering the pharmaceutical composition to a human.

Embodiments disclosed herein also include methods of manufacturing the described pharmaceutical compositions. One such embodiment includes a process for manufacturing a pharmaceutical composition comprising: (a) preparing a solution of 0.05% polysorbate 20 in an aqueous carrier at a predetermined concentration; (b) adding to the solution of step (a) a predetermined amount of a polypeptide having SEQ ID NO:1 or a pharmaceutically acceptable salt thereof, wherein the C terminus is an acid or an amide, and wherein the polypeptide is attached to an organic or inorganic chemical entity that has an anionic charge; (c) adjusting the pH of the solution of step (b) until the polypeptide dissolves in the solution; and (d) if necessary, adjusting the pH of the solution of step (c) to a pH of 5-7, thereby manufacturing the pharmaceutical composition.

Embodiments disclosed herein also include methods of preventing, treating or alleviating the symptoms of an autoimmune or metabolic disorder. One embodiment includes administering a pharmaceutical composition described herein to a human in need of such preventing, treating or alleviating of an autoimmune or metabolic disorder in an amount that is effective to prevent, treat or alleviate the symptoms.

In another embodiment, the disorder is an autoimmune disorder selected from the group consisting of multiple sclerosis, type-1 diabetes mellitus, rheumatoid arthritis, psoriasis, inflammatory bowel disease, contact-mediated dermatitis, psoriatic arthritis, asthma, allergy, restinosis, systemic sclerosis, fibrosis, scleroderma, glomerulonephritis, Sjogren syndrome, inflammatory bone resorption, transplant rejection, graft-versus-host disease, and lupus erythematosis.

In another embodiment, the disorder is a metabolic disorder selected from the group consisting of obesity, Type 2 diabetes, hypercholesterolemia, coronary artery disease, metabolic syndrome, metabolic syndrome X, insulin resistance, hyperlipidemia, lipodystrophy, dyslipidemia, hypertriglyceridemia, glucose intolerance, hypertension, overweightness, and disorders of energy metabolism.

In another embodiment, the pharmaceutical composition is administered daily, weekly, monthly, every two months, every three months, or every six months.

In another embodiment, the pharmaceutical composition is administered subcutaneously.

In a further embodiment, the ShK polypeptide is radiolabeled.

In one embodiment, the ShK polypeptide is labeled with $^{111}$In.

In a further embodiment, the ShK polypeptide is $^{111}$In-labeled ShK-221.

BRIEF DESCRIPTION OF THE FIGURES

FIGS. 1A-1F illustrate biodistribution studies with radiolabeled ShK in rat and squirrel monkey. $^{111}$In-labelled ShK-221 was administered to Sprague Dawley rats (100 µg/kg; 0.7 mCi) and squirrel monkey (35 µg/kg; 0.84 mCi) as a single subcutaneous injection to the scapular region of each animal. SPECT and CT scans were collected continuously during the first hour (4×15 m intervals) and at 4, 8, 24, 48, 72, 120, and 160 hours post-dose. Flattened 2D images of the 3D reconstructions are shown for the 4, 24, 72 and 160 hour time points for monkey (FIG. 1A) and the 1, 8 and 24 hour time points for rat (FIG. 1C). Both animals show slow absorption of drug from the injection site and significant early and sustained distribution to kidney and to a lesser extent liver. Rat images revealed significant radioactivity in bladder at 1 h, the duodenum and small intestine at 4 and 8 hours and adrenal glands at 8 and 24 h. Kidney associated radioactivity in both species was principally identified in the cortex (FIG. 1B and FIG. 1D). Quantification of $^{111}$In-ShK-221 at the injection site in monkey (top) and rat (bottom) revealed a biphasic decay with an initial half-life of approximately 1-1.5 hours and a terminal half-life of >48 hours (FIG. 1E). Drug concentrations in monkey (top) and rat (bottom) whole blood followed a similar biphasic decay with an initial half-life of approximately 1.5 hours and a terminal half-life of >64 hours (FIG. 1F). Blood concentrations remained above the $K_d$ for Kv1.3 throughout the entire study period and above the 80% saturation concentration (233 pM) through the first 120 hours consistent with a slow, continuous distribution from the injection site throughout the study period.

FIG. 2A). Indium incorporation into the DOTA ring was carried out by incubation at 95° C. in sodium acetate pH 5. Indium-labeled ShK-221 yielded a distinct migration pattern by ion-exchange chromatography (FIG. 2B) with the resulting chelates having the expected mass (FIG. 2C).

(FIG. 3A) Representative whole-cell Kv1.3 currents in the absence and presence of ShK-221-Gd. (FIG. 3B) Dose-response curve showing the effect of ShK-186, ShK-221-Gd and ShK-221-In on Kv1.3 currents. Stable Kv1.3-transfected cell lines were used for this study (Beeton, et al. Mol Pharmacol 67:1369-1381 (2005), incorporated by reference herein for its teachings regarding the same). Electrophysiological recordings were carried out in the whole-cell configuration of the patch-clamp technique as described (Beeton, et al. 2005 and Wolff, H, et al., Proc. Natl. Acad. Sci. USA. 97:8151-6 (2000), incorporated by reference herein for its teachings regarding the same). The external solution was sodium Ringer and the pipette solution was KF (300 mOsm). Kv1.3 currents were elicited by 200-ms depolarizing pulses from a holding potential of −80 to 40 mV. ShK-186, ShK-221-Gd and ShK-221-In were each tested at several concentrations. The reduction in peak current at 40 mV for each concentration was used to generate a dose-response curve using Origin software (OriginLab Corp., Northampton, Mass.). The $IC_{50}$ values were: ShK-186=68.99±4.01 pM (n=5), ShK-221-Gd=58.23±1.38 pM (n=5), and ShK-221-In=63.80±2.25 pM (n=3).

DETAILED DESCRIPTION

Figures 1C, 1D:
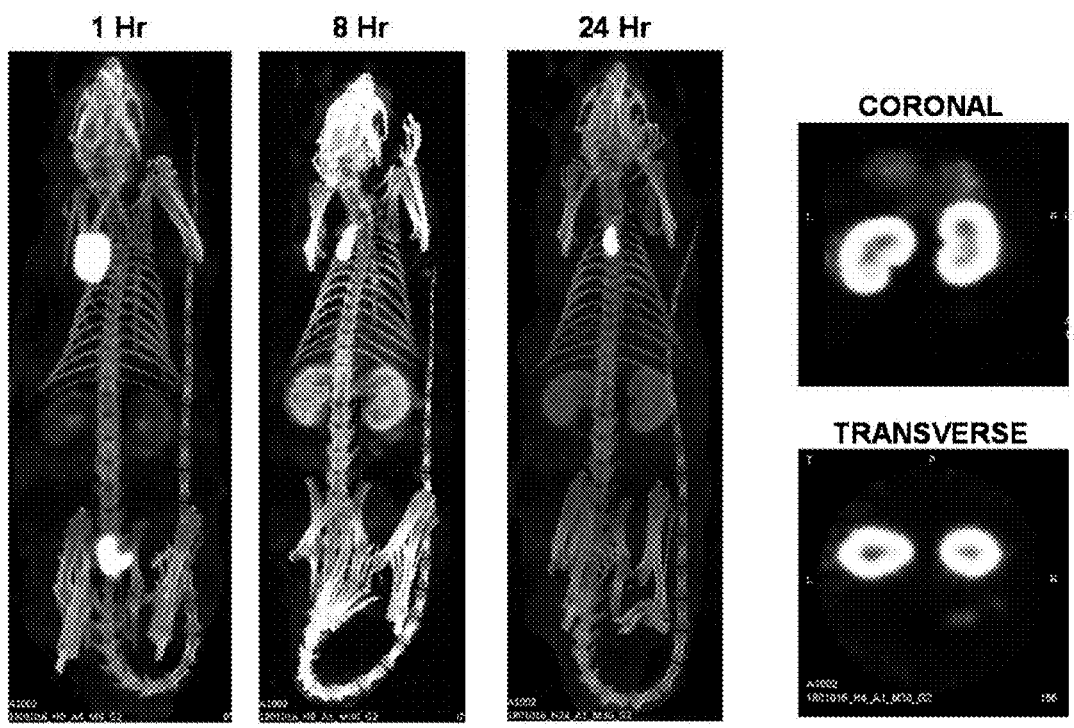

The present disclosure provides ShK-based pharmaceutical compositions and methods of manufacturing and using the same. As used herein, the term "ShK polypeptide" refers to all natural and synthetic ShK polypeptides and their derivatives, analogs, and modifications as contemplated herein. Such modifications and analogs include the polypeptide of SEQ ID NO:1 to which an organic or inorganic chemical entity that has an anionic charge is attached via an aminoethyloxyethyloxy-acetyl linker. As used herein, a "pharmaceutical composition" comprises at least one ShK polypeptide disclosed herein together with one or more pharmaceutically acceptable carriers, excipients or diluents, as appropriate for the chosen mode of administration. The "at least one ShK polypeptide" can include both natural and synthetic ShK polypeptides.

As stated, many immune-related human diseases and metabolic disorders are attributed to the action of memory T cells. Two categories of memory T cells are known: central memory T cells ($T_{CM}$) and effector memory T cells ($T_{EM}$). Upon activation, $T_{EM}$ cells up-regulate Kv1.3 K$^+$ ion channels. The antigen-driven proliferation of $T_{EM}$ cells is sensitive to Kv1.3 K$^+$ ion channels blockers (Wulff et al., J. Clin. Invest. 111:1703-1713, 2003), and the polypeptide ShK, originally isolated from the Caribbean sea anemone *Stichodactyla helianthus*, serves as such a blocker. By blocking Kv1.3 channels, ShK suppresses proliferation of $T_{EM}$ cells at picomolar concentrations.

Myelin-specific autoreactive T cells in MS patients are predominantly activated $T_{EM}$ cells (Wulff et al., J. Clin. Invest. 111:1703-1713, 2003), so although the compositions disclosed herein are not bound by a specific mechanism, there is a sound basis for preparing Kv1.3 blockers as pharmaceutical compositions to reduce or eliminate activation of $T_{EM}$ cells in the treatment, prevention or alleviation of symptoms in multiple sclerosis patients.

A native ShK polypeptide is described in, for example, Pennington, M. W. et al., Int. J. Pept. Protein Res. 46:354-358 (1995) which is incorporated by reference herein for its teachings regarding the same. Exemplary ShK structures that are within the scope of the present disclosure are also published in Beeton, C. et al., Targeting Effector Memory T Cells with a Selective Peptide Inhibitor of Kv1.3 Channels for Therapy of Autoimmune Diseases, Molecular Pharmacology, Vol. 67:1369 (2005), and in U.S. Pat. No. 8,080,523 (U.S. Patent Publication 20080221024), all of which are incorporated herein by reference for their teachings regarding the same.

An exemplary polypeptide that forms the basis for the polypeptides used in the compositions herein is shown in SEQ ID NO:1. In particular embodiments, the C-terminus is an acid (for example, COOH) or an amide (for example, CONH2), and the polypeptide is attached to an organic or inorganic chemical entity that has an anionic charge. By "amide" it is meant the substitution of the C-terminal hydroxyl group (OH) of an acid with $NH_2$. Such substitution is designated herein using the term "amide," or as the C-terminal amino acid-$NH_2$, as in "-Cys-$NH_2$."

The safety, potency, and specificity of ShK has been investigated and attaching the polypeptide to an organic or inorganic chemical entity that has an anionic charge has been shown to improve the suitability of ShK for use in pharmaceutical compositions.

Those skilled in the art are aware of techniques for designing ShK polypeptides with enhanced properties, such as alanine scanning, rational design based on alignment mediated mutagenesis using known ShK polypeptide sequences and/or molecular modeling. For example, ShK polypeptides can be designed to remove protease cleavage sites (e.g., trypsin cleavage sites at K or R residues and/or chymotrypsin cleavage sites at F, Y, or W residues) in a ShK polypeptide-containing composition.

A variety of modifications of the SEQ ID NO:1 polypeptide are suitable. A polypeptide can have any combination of the modifications disclosed herein. To improve the pharmacokinetic and pharmacodynamic (PK/PD) properties of the ShK structure, residues that are sensitive to degradation properties can be replaced or substituted. For example, the Met residue at position 21 can be substituted to impart a stabilizing effect against oxidation. In one embodiment, the Met at position 21 is substituted with Nle. Substitution of the C-terminal acid function with an amide can also impart stability. These two substitutions to the primary structure of ShK can be combined with an anionic moiety at the N-terminus to produce a stable and selective Kv1.3 blocker. Accordingly, one embodiment disclosed herein includes SEQ ID NO:1 wherein the methionine at position 21 is substituted with Nle, an amide is present at the C-terminus and/or an anionic moiety is present at the N-terminus.

Nonhydrolyzable phosphate substitutions also impart a stabilizing effect on the phosphate groups, as well as stability against phosphatase enzymes.

As stated, certain embodiments include the attachment of an organic or inorganic chemical entity. The site of attachment can be the N-terminus, (the first Arg in SEQ ID NO:1), but modifications are not limited to attachment at this site. Exemplary chemical entities can be attached by way of a linker, such as an aminoethyloxyethyloxy-acetyl linker (referred to herein interchangeably as Aeea or AEEAc), or by any other suitable means.

Non-limiting examples of appropriate chemical entities include L-Pmp($OH_2$); D-Pmp($OH_2$); D-Pmp(OHEt); Pmp($Et_2$); D-Pmp($Et_2$); L-Tyr; L-Tyr($PO_3H_2$) (p-phospho-Tyrosine); L-Phe(p-$NH_2$); L-Phe(p-$CO_2H$); L-Aspartate; D-Aspartate; L-Glutamate; and D-Glutamate. The abbreviations used are defined as follows: Pmp (p-phosphonomethyl-phenylalanine); and Ppa (p-phosphatityl-phenylalanine). Alternatives to PmP and Ppa include, without limitation, Pfp (p-Phosphono(difluoro-methyl)-Phenylalanine) (Pfp) and Pkp (p-Phosphono-methylketo-Phenylalanine).

Non-limiting examples of chemical entity/linker combinations include AEEAc-L-Pmp($OH_2$); AEEAc-D-Pmp($OH_2$); AEEAc-D-Pmp(OHEt); AEEAc-L-Pmp($Et_2$); AEEAc-D-Pmp($Et_2$); AEEAc-L-Tyr; AEEAc-L-Tyr($PO_3H_2$); AEEAc-L-Phe(p-$NH_2$); AEEAc-L-Phe(p-$CO_2H$); AEEAc-L-Aspartate; AEEAc-D-Aspartate; AEEAc-L-Glutamate; and AEEAc-D-Glutamate. In the chemical entities generally, where the amino acid residue has a chiral center, the D and/or L enantiomer of the amino acid residue can be used.

For use in the disclosed pharmaceutical compositions, ShK polypeptide can be naturally occurring or synthetic or be provided as a mixture of naturally occurring and synthetic ShK.

The ShK polypeptide can be prepared as a salt. In an exemplary salt herein, the refolded polypeptide obtained from the RP-HPLC step (Example 1) can be returned to the column and eluted. Before drying, sodium or potassium acetate at 50 mM can be added to the protein solution. This step yields a salt form of the protein which is readily soluble upon reconstitution from the dried form. In the exemplary formulation used in the Examples (ShK-186), sodium acetate was added, and the acetate content of the formulation was 10.4% by weight, by chemical analysis. ShK-186 is a 37 amino acid synthetic peptide derivative of the *Stichodactyla* toxin. ShK-186 has also been referred to as SL5 in the literature and is identified by CAS Registry Number 1081110-69-1.

For a polypeptide-containing composition to find use as a pharmaceutical composition, it must meet several criteria in terms of stability, solubility, and pH, and preferably only contain materials consistent with administration to animals including, without limitation, mammals, and particularly humans. The composition can be varied depending on the mode of administration, such as subcutaneous, intravenous, etc.

Although some formulations of therapeutic ShK polypeptides are known in the art (for example, Beeton, C. et al., referenced above; and U.S. Pat. No. 7,833,979), none have the stability and solubility of the ShK-based pharmaceutical compositions disclosed herein. The stable and soluble ShK-based pharmaceutical compositions disclosed herein were achieved through varying a number of factors including surfactant concentrations, pH, removal of components used in previous formulations and other parameters described more fully in the Examples below.

One particular formulation with optimal stability and solubility includes:

TABLE 1

Pharmaceutical composition of P6N formulation

| Component | Concentration | Purpose |
|---|---|---|
| ShK-186 polypeptide | Up to 500 mg/mL | Active agent |
| Sodium phosphate | 10 mM | Buffering agent |
| NaCl | 150 mM | Tonicity modifier |
| Polysorbate 20 | 0.05% (w/v) | Surfactant | pH of 6.0

Therapeutically and prophylactically effective amounts of the disclosed pharmaceutical compositions as well as dosage regimens for treating, preventing and/or alleviating symptoms of an autoimmune disorder or metabolic disorder can be determined by an attending physician, considering various factors such as the age, condition, body weight, sex and diet of the patient, the severity of the condition being treated, time of administration, and other clinical factors. Generally, the daily amount or regimen should be in the range of 1 to 10,000 micrograms (μg) of the ShK polypeptide per kilogram (kg) of body mass, in the range of 1 to 5,000 μg per kilogram of body mass, in the range of 1 to 1,000 μg per kilogram of body mass or in the range of 1 to 100 μg per kilogram of body mass.

Pharmaceutical compositions disclosed herein can be used to treat autoimmune-related disorders such as multiple sclerosis, type-1 diabetes mellitus, rheumatoid arthritis, psoriasis, inflammatory bowel disease, contact-mediated dermatitis, psoriatic arthritis, asthma, allergy, restinosis, systemic sclerosis, fibrosis, scleroderma, glomerulonephritis, Sjogren syndrome, inflammatory bone resorption, transplant rejection, graft-versus-host disease, and lupus erythematosis and metabolic disorders such as obesity, Type 2 diabetes, hypercholesterolemia, coronary artery disease, metabolic syndrome, metabolic syndrome X, insulin resistance, hyperlipidemia, lipodystrophy, dyslipidemia, hypertriglyceridemia, glucose intolerance, hypertension, overweight, and disorders of energy metabolism.

For long-term storage of the pharmaceutical compositions, it can be useful to store them in lyophilized form. The present disclosure encompasses such lyophilized pharmaceutical compositions including but not limited to those prepared by the processes described below.

One process of lyophilizing can comprise the steps of: (a) lowering the temperature of the pharmaceutical composition to −40° C.; (b) holding the temperature at −40° C. for a predetermined time; (c) raising the temperature of the solution to 20° C.; (d) holding the temperature at 20° C. for a predetermined time; and e) reducing the pressure in step (d) to a pressure suitable for lyophilization and holding the temperature at 20° C. for a predetermined time, thereby lyophilizing the pharmaceutical composition.

In this process of lyophilization, step (a) can be performed within 2 hours; step (b) can be performed within 3 hours; step (c) can be performed over 13 hours and at a pressure of 110 pbar; step (d) can be performed over 13 hours and at a pressure of 110 µbar; and step (e) can be performed over 5 hours and the pressure is reduced to 10 µbar.

The process of lyophilizing the pharmaceutical composition can also comprise the steps of: (a) lowering the temperature of the pharmaceutical composition to −45° C.; (b) holding the temperature at −45° C. for a predetermined time; (c) raising the temperature of the solution to −20° C.; (d) raising the temperature of the solution to 25° C.; and (e) holding the temperature at 25° C. for a predetermined time, thereby lyophilizing the pharmaceutical composition.

In this process, step (a) can be performed within 6 hours; step (b) can be performed within 3 hours; step (c) can be performed over 19 hours and at a pressure of 150 µbar; step (d) can be performed over 13 hours and at a pressure of 150 µbar; and step (e) can be performed over 8 hours and at a pressure of 150 µbar.

The lyophilized pharmaceutical composition can be contained within packaging material, and the packaging can further comprise instructions for reconstitution of the pharmaceutical composition for end-use by a medical professional, patient, or researcher.

The lyophilized pharmaceutical composition can have a water content of less than 5%, less than 4%, or less than 3.5%.

As indicated in the Examples below, the pharmaceutical compositions can be stored for several months at −70° C., −20° C., or 4° C., for example in a sterile glass vial. A vial can contain 1 ml of composition P6N (see Table 1) or another pharmaceutical composition disclosed herein, such that the vial will physically contain a solution of 50 mg ShK polypeptide (in one embodiment as an acetate salt), dissolved in 10 mM sodium phosphate and 150 mM NaCl, with 0.05% (w/v) polysorbate 20, and with the final pH adjusted to 6.0.

The vial can be further prepared as a unit of pharmaceutical manufacture, with one or more vials in a package that can also contain or be printed with instructions for storage, and for diluting and administering the pharmaceutical composition, for end-use by a medical professional, patient, or researcher. A suitable mode of diluting includes the use of water for injection, referred to herein as WFI. A suitable amount of diluent can be part of the unit of manufacture, for example in its own sterile container with optional instructions for use.

The pharmaceutical composition can comprise 0.1, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 or 55, or up to 500 mg/ml of the ShK polypeptide or pharmaceutically acceptable salt thereof according to this disclosure. The precise concentration will depend on factors within the control of the manufacturer and/or the end-user, depending upon desired dose and intended therapeutic or research use. The concentration also encompasses any and all intermediate numbers within the above range, such as 1.5 mg/ml, 2.5 mg/ml, etc.

For administration of the pharmaceutical composition, a suitable route is subcutaneous injection. A medical practitioner will be familiar with methods of administration depending on the patient and the mode of treatment, such as subcutaneous, intravenous, etc. U.S. Pat. No. 7,918,824 discloses syringes suitable for patient use and is incorporated by reference herein for its teachings regarding the same. Intravenous administration is also contemplated. For example, pre-filled needleless syringes, such as glass syringes, for use with needleless intravenous access systems can be used. Also contemplated are implantable devices for timed release of the pharmaceutical compositions. The compositions are not intended to be limited to any particular choice of administration.

The disclosure, for example, encompasses drawing the pharmaceutical composition in liquid form, for example 0.5 cc, into a syringe, such as a Becton Dickinson (BD) Slip-Tip Sub-Q 1 cc syringe fitted with a 26G×⅝ inch needle (BD Part #309597). One or more syringes can be incorporated into a unit of manufacture, including packaging and optional instructions for end-use by a medical professional, patient, or researcher.

The pharmaceutical compositions can be made up in, without limitation, a solid form (including granules, powders or suppositories) or in a liquid form (e.g., solutions, suspensions, or emulsions). The pharmaceutical compositions can be subjected to conventional pharmaceutical operations such as sterilization and/or can contain conventional adjuvants, such as preservatives, stabilizers, wetting agents, emulsifiers, buffers, etc.

Solid dosage forms for oral administration can include capsules, tablets, pills, powders, and granules. In such solid dosage forms, the active ShK polypeptide can be admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting, sweetening, flavoring, and perfuming agents. The pharmaceutical composition can contain more than one embodiment of the present disclosure. Preparations for oral administration can be suitably formulated to give controlled release of the active ShK polypeptide.

For buccal administration the compositions can take the form of tablets or lozenges formulated in conventional manner.

The ShK polypeptides can be formulated for parenteral administration by injection e.g. by bolus injection or infusion. Formulations for injection can be presented in unit dosage form, e.g. in glass ampoule or multi dose containers, e.g. glass vials. The compositions for injection can take such forms as suspensions, solutions or emulsions in oily or aqueous vehicles, and can contain formulatory agents such as suspending, stabilizing, preserving and/or dispersing agents. Alternatively, the active ingredient can be in powder form for constitution with a suitable vehicle, e.g. sterile pyrogen-free water, before use.

In addition to the formulations described above, the ShK polypeptides can also be formulated as a depot preparation. Such long acting formulations can be administered by implantation or by intramuscular injection.

For nasal or pulmonary administration or any other administration by inhalation, the ShK polypeptides for use according to the present disclosure are conveniently delivered in the form of an aerosol spray presentation for pressurized packs or a nebulizer, with the use of suitable propellant, e.g. dichlorodifluoromethane, trichlorofluoromethane, dichlorotetrafluoroethane, carbon dioxide or other suitable gas or mixture of gases.

In a non-limiting example, a ShK polypeptide disclosed herein can be labeled using a 1,4,7,10-tetraazacyclododecane-1,4,7,10-tetraacetic acid (DOTA)-chelate of Indium-111 ($In^{111}$) or other radiolabeled metal conjugated to a tyrosine or phosphotyrosine moiety on the polypeptide. Such methods are described in, for example, Schultz, M. K. et al., "Synthesis of a DOTA-Biotin Conjugate for Radionuclide Chelation via Cu-Free Click Chemistry," *Organic Letters* 12:2398-2401 (2010) which is incorporated by reference herein for its teachings regarding the same. In an example suitable for diagnosis, such as by MRI, a ShK polypeptide disclosed herein can be labeled using a DOTA-chelate of indium (In), gadolinium (Gd) or other paramagnetic ion. Other chelation or conjugation chemistries can also be used.

As described in Example 6 and illustrated in FIGS. 1A-3B, a radiolabeled analog of ShK (ShK-221) was used to measure the total drug concentration (unbound plus bound) in whole blood. Previous studies suggest that only 10% of the drug is available unbound in plasma (Chi et al., *Toxicon* 59:529-46, 2011). This is consistent with the observation that at 1 hour after administration of a 35 µg/kg dose of radiolabeled ShK-221 to squirrel monkey, approximately 15 nM of drug was measured in whole blood, suggesting an unbound fraction of ~7% by this method. The free fraction of the drug may actually be lower in the rat compared to non-human primates. At 1 hour post dose of 100 µg/kg in rats, approximately 14 nM of ShK-221 was observed in whole blood. This may be due to the drug binding to other blood constituents such as platelets, which express Kv1.3 on their surface and have been found to be present in exceedingly high numbers in rat whole blood (5-10×Human) (McCloskey et al., *J. Physiol.* 588:1399-406, 2010; Trowbridge et al., *Clin. Phys. Physiol. Meas.* 5:145-70, 1984).

The sensitive radiolabeling method allows the detection of a biphasic terminal elimination profile for ShK in rat and squirrel monkey species characterized by a rapid initial phase and a very long terminal phase. The terminal half-life computed using $^{111}$In-ShK-221 was >64 hours in monkey with sustained blood levels above the $K_d$ for 7 days. The blood concentrations mimic a biphasic (fast then slow) absorption from the injection site. In summary, the biodistribution of radiolabeled ShK-221 in rat and squirrel monkey is characterized by a very slow distribution from the injection site, significant concentrations of drug peripherally in the injection site, kidney, and liver, and a long terminal elimination phase in whole blood. Drug levels remained above ~200 pM in blood for approximately 7 days in the monkey and 3 days in the rat. The data in Example 1 provide one embodiment of the use of a radiolabeled ShK polypeptide to study the distribution of the drug in vivo. DOTA is exemplified herein, but other metal chelators can be used, such as DTPA (diethylenetriaminepentaacetic acid). Thus, in addition to therapeutic uses, the ShK polypeptides disclosed herein can also be useful in diagnosing or monitoring diseases characterized by dysfunction of their associated protein of interest. In one embodiment, a method is provided for detecting a protein of interest in a biological sample, such as a receptor or ion channel that is capable of being affected, comprising the steps of: (a) contacting the sample with a ShK polypeptide; and (b) detecting an effect on the protein of interest by the peptide. The biological samples include tissue specimens, intact cells, or extracts thereof. The compositions disclosed herein can be used as part of a diagnostic kit to detect the presence of their associated proteins of interest in a biological sample. Such kits can employ a composition disclosed herein and having an attached label to allow for detection. The peptides are useful for identifying normal or abnormal proteins of interest.

The Examples below describe the optimization of the methods disclosed herein. The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1. Synthesis of (pTyr)-AEEA-Arg-35-Cys-NH$_2$ (ShK-186)

Synthesis of the linear polypeptide precursor was carried out as follows. The linear peptide was assembled on Rink Amide (MBNA) Rx (sub: 0.4 mmol/g) and the following protecting groups were used for the Fmoc-chemistry: Arg (Pbf), Ser (tBu), Cys (Trt), Asp (OtBu), Thr (tBu), Lys (Boc), Arg (Pbf), Gln (Trt), His (Trt), Tyr (tBu), and Tyr (P(OH)O$_2$Bzl). All amino acids were coupled by DIC/HOBt activation at a scale of 2 mmol using CS536 automated synthesizer. These parameters were scaled up to 200 mmol.

For the cleavage step, the DeFmoc peptide was finally cleaved from the resin by 4-hour treatment of Reagent 'K' [TFA/TIS/1,2-Ethanedithiol (EDT)/H$_2$O/Phenol (89/2/2/2/5)] at room temperature with stirring. (TIS refers to triisopropylsilane.) The ratio can be varied as long as the cleavage is accomplished, and phenol can be optionally eliminated. In preparations without phenol, the ratio of TFA/TIS/EDT/H$_2$O was, for example, 47/1/1/1. The crude peptide was separated from the resin by SPE tube filtration and the resin was rinsed consecutively with TFA which was combined with the initial filtrate.

After evaporation of TFA solvents from the filtrate (to ⅕ volume of original cleavage cocktail), the crude peptide was then precipitated by addition of cool ethyl ether and dried in vacuum to give linear polypeptide for further oxidation.

After linear crude polypeptide was dissolved in water to a concentration of 0.3 mg/mL (changed slightly based on manufacture), NH$_4$OH was then added to execute oxidization at pH 8 (later batch records show lower pH (7-7.5)) for 30 hours. The completion of oxidization was checked by ESI mass spectrum. Additionally, the HPLC analysis showed the conversion of the linear peptide to the oxidized form. The oxidation was acidified by TFA (or acetic acid) to pH (2-)3. Air oxidation is one method of achieving disulfide bridge formation. Example 2 below shows an alternative manner of obtaining the polypeptide with disulfide bonds.

For purification, the oxidized peptide was directly loaded and purified by RP-HPLC on a preparative C-18 column using acetonitrile as the mobile phase. Fractions with enough purity were combined and optionally lyophilized to give a white powder (ShK-186), 1.5 g (TFA salt).

A salt exchange step followed. The re-dissolved peptide (TFA salt) was loaded on a prep C-18 column balanced by TEAP (triethylamine phosphate) 20 mM. After 3× void volume washing with TEAP, the buffer was changed to NH$_4$OAc (50 mM). After 3× void volume washing of NH$_4$OAc and pH checking (pH 6-7), the buffer was changed to HOAc (0.5%). After washing 3× void volume of HOAc (0.5%) and pH checking (pH 2-3), a sharp gradient was started to give the final polypeptide with acetate salt, 500 mg.

An optional purification step can be performed. The polypeptide can be purified directly using an acetic acid system to give the final polypeptide with a higher yield. All of the individual steps in the above process can be performed in batch to yield a larger overall scale. The final product can be lyophilized or maintained in solution.

Example 2. Preparation of ShK Polypeptides

Anionic amino acid residues can be attached to the N terminus of natural or synthetic ShK polypeptide by way of a linker, such as an aminoethyloxyethyloxy-acetyl linker (Aeea), or by any other suitable means. Initially, Fmoc-Aeea-OH is coupled to the N-terminus of natural or synthetic ShK toxin, for example by the method of Beeton, C. et al., 2005.

Either Fmoc-Tyr(PO$_4$Bzl)-OH, Fmoc-d-Tyr(PO$_4$Bzl)-OH, Fmoc-Tyr(PO$_4$Me$_2$)—OH, Fmoc-Pmp-OH, Fmoc-d-Pmp-OH, Fmoc-Pmp(Et)—OH, Fmoc-Pmp(Et)$_2$-OH, Fmoc-Tyr(tBu)—OH, or Fmoc-Amp(Boc)-OH is then coupled using DIC and HOBT.

The deblocked peptide resin is then cleaved and deprotected with Reagent K containing 5% triisopropylsilane for 2 hours at RT as described in King, D. S. et al., Int. J. Peptide Protein Res. 36, 255-266, 1990 which is incorporated by reference herein for its teachings regarding the same. Met (O) is reduced by addition of solid NH$_4$I to the cleavage cocktail at t-15 min. (Nicolas, E. et al., Tetrahedron 51:5701-5710, 1995 which is incorporated by reference herein for its teachings regarding the same). For the peptide containing Tyr(PO$_4$Me$_2$)—OH, a cleavage cocktail containing 1 M TMSBr in TFA containing thioanisole as a scavenger for 18 hr at 4° C. is used (Tian, Z. et al., Int. J. Peptide Protein Res. 42:155-158, 1993 which is incorporated by reference herein for its teachings regarding the same). Incomplete removal of the methyl protecting groups is common when using this method and two of the species (Tyr(PO$_4$) and Tyr(PO$_4$Me)) are easily purified by RP-HPLC.

The Tyr(PO$_4$Me$_2$)-containing polypeptide is cleaved via standard Reagent K cleavage keeping both Me groups intact. In each case, the cleavage mixture is filtered and the crude peptide is precipitated into ice-cold diethyl ether. The precipitate is collected, yielding approximately 75 mg of peptide from 200 mg of resin. The crude product is dissolved in 20 ml of 50% aqueous AcOH and diluted into 0.75 l of H$_2$O. The pH of the solution is adjusted with NH$_4$OH to 8.2, and it was allowed to fold overnight with the addition of glutathione (2 mM:1 mM) (reduced:oxidized).

All polypeptides are purified using RP-HPLC as described in Pennington, M. et al., Int. J. Peptide Protein Res. 546:354-358, 1995; Pennington, M. et al., Biochemistry 35: 16407-16411, 1996a; and Pennington, M. et al., Biochem. Biophys. Commun. 219:696-701, 1996b, each of which is incorporated by reference herein for its teachings regarding the same. Pure fractions are pooled and lyophilized. Each sample is confirmed by RP-HPLC, AAA (amino acid analysis) and MALDI-TOF MS and adjusted to account for peptide content prior to bioassay.

In the Examples below, the ShK polypeptide identified as ShK-186 ((phospho-Tyr)-AEEA-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-NH$_2$, with amide at the C-terminus and with disulfide bonds between Cys3-Cys35, Cys12-Cys28, and Cys17-Cys32) (SEQ ID NO:2) was prepared and chosen for identifying the components of a suitable pharmaceutical composition; these components can be used for preparing pharmaceutical compositions comprising other ShK polypeptides, including but not limited to ShK-198 and ShK-192 (CAS Registry Number 1159528-26-3).

Example 3. Surfactant Screening

In order to identify surfactant(s) for possible inclusion in the pharmaceutical compositions, the polypeptide is formulated in buffer, to which test surfactants are added individually, and compared with samples having no surfactant. Surfactants tested include polysorbate 20, polysorbate 80, and pluronic F68 at concentrations beginning with 0.01%.

To determine the effect of the surfactant, test samples and controls are subjected to agitation or no agitation. Test samples and controls are then analyzed by size-exclusion-HPLC (SEC-HPLC or SE-HPLC) to monitor changes in characteristics, including soluble aggregation and loss of monomer recovery.

Using this method, ShK-186 polypeptide preparations were subject to constant agitation for up to four hours at pH 5.8, in the presence of polysorbate 20 (0.01%), polysorbate 80 (0.01%), or pluronic F68 (0.10%) (Sigma-Aldrich). Surprisingly, all samples showed haziness with increased turbidity, with or without surfactant. This suggested that ShK-186 was susceptible to agitation-induced precipitation.

Additional experimentation indicated that a non-typical concentration of surfactant protected the protein, and for subsequent experiments, polysorbate 20 at a concentration of 0.05% was used. In addition to increasing the concentration of surfactant, lowering the pH from 5.8 to 5.1 further improved the stability of ShK-186. The absence of soluble aggregation was confirmed by SEC-HPLC.

Example 4. Stability During Storage

Several parameters are tested in order to choose components of the pharmaceutical compositions that will protect the stability of the polypeptide. According to the present method, these parameters are pH (4.0-7.0), buffer/solvent (10 mM Na acetate or 10 mM Na phosphate), stabilizer/solubilizer (NaCl 0.8%; sorbitol 5.0%; L-Arginine 3.0%), surfactant, storage and stress conditions (temperature, agitation, freeze/thaw, forced oxidation).

To study these parameters, samples of ShK-186 were dissolved in Na acetate or Na phosphate, and individual formulations were prepared as described above. The peptides were then analyzed at time zero using reversed-phase HPLC (RP-HPLC), ion-exchange HPLC (IE or IEX-HPLC), and size-exclusion HPLC (SE-HPLC). Additional analysis was performed at two-week, four-week, and eight-week time points. The evaluation of the formulations included monitoring drug concentration, visual inspection/turbidity, and checking pH over time at 10 and 25 mg/mL.

At time zero, the samples showed similar SE-HPLC chromatographs, except for the sample prepared in phosphate buffer with arginine, pH 7.

At week two, the formulation containing arginine showed a turbid solution with precipitates. This result was unexpected, as arginine has been used to enhance the solubility of other protein products. Similar solubility issues were observed at other temperatures, so the arginine-containing formulation was excluded from further analyses. At four weeks, SE-HPLC analysis showed that all remaining formulations showed no sign of soluble aggregate or cleavage at temperatures below 25° C.

At week eight, all but one of the formulations showed good stability during storage at −70° C.

Results from the full analysis at week eight led to the selection of a formulation referred to herein as "P6N" for providing the best stability in terms of recovery and degradation as observed by RP-HPLC, IE-HPLC, and SE-HPLC. This formulation, at pH 6, contains 10 mM Na acetate as buffer; 0.8% NaCl as stabilizer/tonicity modifier; 0.05% polysorbate 20 as surfactant; and a concentration of protein 11.2 mg/mL as determined by RP-HPLC. The concentration of protein could be increased to 50 mg/mL.

The P6N formulation showed no sign of change after five cycles of freeze-thawing, as determined by RP-HPLC and IEX-HPLC. After three hours of vigorous vortex stress, this formulation remained clear with no sign of degradation, as determined using RP-HPLC and IE-HPLC.

Example 5. Stability of Clinical Formulation

The short-term stability of ShK-186 formulated in P6N is studied in three sets of conditions designed to replicate clinical use: 72-hour storage at variable temperatures, and 24-hour storage in sterile plastic syringes. Long-term stability is tested over 1, 3, 6 and 12 months of storage at refrigerated (such as 5° C.) and freezing (such as −70° C., −20° C.) temperatures.

For short-term studies, ShK-186 is diluted to a final concentration of 1 mg/ml using either 5% (w/v) dextrose or 0.9% (w/v) saline, or WFI solutions. A short-term stability study spans 72 hours of storage at refrigerated (such as 5° C.) and elevated (such as 40° C.) temperatures in each diluent. ShK-186 diluted in WFI, without preservatives, serves as a control. For long-term studies, ShK-186 is formulated in P6N at either 25 or 50 mg/ml, then aliquots are used to prepare samples having a final concentration as indicated, in mg/ml. Experimental parameters are shown in Tables 2 and 3.

TABLE 2

Diluent Stability Study, short term

| Final ShK-186 concentration, mg/ml | Diluent | Storage temperature, centigrade | Time points, in hours |
|---|---|---|---|
| 1 | 5% (w/v) Dextrose in WFI | 5, 25, 40 | 0, 24, 72 |
| 1 | 0.9% (w/v) NaCl in WFI | | |
| 1 | WFI (control) | | |

TABLE 3

Diluent Stability Study, long term

| Final ShK-186 concentration, mg/ml | pH | Buffer, 10 mM | Stabilizer, w/v | Storage temperature, centigrade | Time points, in months |
|---|---|---|---|---|---|
| 25 | 6.0 | Na phosphate | 0.8% NaCl | −70, −20, +5 | 0, 1, 3, 6, 12 |
| 10 | 6.0 | Na phosphate | 0.8% NaCl | | |

A stability study performed at six months as shown in Table 3 yielded the following results based on SEC-HPLC and RP-HPLC. There was no significant change in pH or concentration at six months, compared to earlier time points. The overall results indicated that peptide concentrations did not show any significant impact on stability of formulations. Stability at 5° C. showed a very slight drop compared to −20° C. and −70° C. Such results are consistent with the industry standard of storing polypeptide pharmaceutical compositions at low temperatures, at least below freezing.

The stability in a delivery device such as a sterile plastic 1 cc syringe is characterized. Such a device is suitable for subcutaneous delivery. An exemplary, non-limiting device is a Becton Dickinson (BD) Slip-Tip Sub-Q 1 cc syringe fitted with a 26 G×⅝ inch needle (BD Part #309597). 0.5 ml aliquots of ShK-186 formulation in diluents and concentration shown in Table 2 are drawn and incubated in the syringe at ambient conditions. Stability is tested over time reflecting clinical use, for example at four hours.

The stability of ShK-186 at three concentrations, 10, 25, and 50 mg/ml, under refrigerated and frozen storage temperatures is determined. Lyophilized ShK-186 is dissolved in P6N formulation to achieve these final concentrations of ShK-186. Each formulated solution is sterilized with 0.2 μm filters, and transferred into suitable sterile vials, such as type I borosilicate glass 3 cc vials at a fill volume of 0.5 ml per vial, under sterile conditions. The vials are stored at 5° C., −20° C., and −70° C. for testing at time points of zero, three and six months.

The samples are tested at the designated time points using the parameters shown in Table 4.

TABLE 4

Analytical Methods to Monitor ShK-186 Stability

| Analytical method | Evaluation result |
|---|---|
| Visual inspection | Appearance |
| pH | pH value |
| Osmolality | Osmolality value |
| UV-Vis spectrophotometry | Concentration (Abs 280 mm) |
| | Turbidity (Abs 500-700 nm) |

TABLE 4-continued

Analytical Methods to Monitor ShK-186 Stability

| Analytical method | Evaluation result |
|---|---|
| Size exclusion HPLC | Purity, aggregates, cleavage |
| Reversed phase HPLC | Purity, chemical modifications |
| Bioassay | Potency/strength of polypeptide |

Summary. The Examples above provide methods for determining suitable components and conditions for preparing pharmaceutically acceptable compositions comprising a ShK polypeptide for therapeutic use. The validity of the methods was demonstrated by the successful preparation of ShK-186 in a formulation that provides for good solubility, long-term storage (six months), and stability.

Example 6. Twelve Month Stability Study

SkH-186 was formulated at 10 mg/ml and 25 mg/ml in 10 mM Sodium Phosphate, pH 6.0, containing 0.8% NaCl and 0.05% Polysorbate 20, and incubated for 12 months at 5° C., −20° C., and −70° C. SE-HPLC analysis indicated that the concentration of the formulations did not have any obvious impact on their stability. Incubation temperature had a slight impact on the stability of both formulations. Samples incubated at 5° C. revealed a small increase in % HMV (1.19%) compared to frozen samples (0.95%). The percentage of LMW species remained relatively unchanged for both formulations at all temperatures. Based on SE-HPLC results, the overall percentage of monomer for both formulations at the end of the study was about 98%.

RP-HPLC analysis of the samples also indicated that the concentration of formulations did not have any obvious impact on the stability of formulations. Samples incubated at 5° C. revealed a slight increase in pre- and post-peak degradations (0.8-0.9%) compared to frozen formulations (0.3-0.7%). The data indicated that the higher incubation temperature resulted in a higher percentage of post-peak degradation compared to pre-peak degradation. Based on RP-HPLC results, the overall purity for both formulations at the end of the study was about 99%.

Table 5 shows a summary of pH and concentration data collected throughout the timeframe of the 12-month study. At Time Zero, the values were as follows: for 10P6N (ShK-186 at 10 mg/mL), the pH was 6.1, Concentration (Conc, mg/mL) was 9.9 mg/mL, and Osmolality in mOsmo was 317. For 25P6N (ShK-186 at 25 mg/mL), the pH was 6.0, Concentration was 25.1 mg/mL, and Osmolality was 293. Based on the results, the pH and concentration of samples remained relatively unchanged throughout the study regardless of incubation temperature.

Example 7. Biodistribution of Radiolabeled ShK-221

Introduction. In order to enhance the sensitivity of in vivo studies, measure the biodistribution of ShK-186, and evaluate the total (bound plus unbound) drug concentration in whole blood, a radiolabeled analog of ShK-186 was prepared and studied in two in vivo animal models, rat and squirrel monkey. In this Example, the term "ADME" refers to absorption, distribution, metabolism, excretion.

Methods.

Animals. Sprague Dawley [Crl:CD® SD] rats (6-9 weeks old) were purchased from Charles River Laboratories (Wilmington, Mass., USA) and housed in a temperature (64-79° C.) and humidity (30-70%) controlled facility. Food and water were ad libitum.

Non-naïve squirrel monkeys (Saimiri boliviensis) were between 2 and 5 years of age and were transferred from the MPI Research (Mattawan, Mich., USA) stock colony. The squirrel monkey was of Bolivian origin and provided by the University of Texas MD Anderson Cancer Center (Houston, Tex. USA). Animals were housed individually in stainless steel cages in an environmentally controlled room. The monkeys were provided environmental enrichment; fluorescent lighting was provided 12 hours per day. Temperature was maintained between 64 and 84° C.; humidity was 30-70%. Animals were provided Certified Primate Diet (PMI Nutrition International, Inc., St. Louis, Mo., USA) twice daily. Primatreats® and other enrichment foods were provided on a regular basis. Water was available ad libitum.

DOTA-conjugate of ShK-186 (ShK-221). "DOTA" refers to 1,4,7,10-tetraazacyclododecane-1,4,7,10-tetraacetic acid. ShK-221 (MW 4442) was synthesized using an Fmoc-tBu solid-phase strategy. Briefly, the peptide was assembled using a Chem-Matrix amide resin at a 0.2 mmol scale. All of the coupling steps were mediated with 6-CI-HOBt (N-Hydroxybenzotriazole) in the presence of diisopropyl carbodiimide. Fmoc removal was facilitated with 20% piperidine in DMF (dimethylformamide) containing 0.1 M HOBt to buffer the piperidine and minimize potential racemization at the 6 Cys residues. The DOTA(tBu)3-OH was coupled to the N-terminus using the same aforementioned coupling protocol. Following assembly, the peptide was cleaved from the resin and simultaneously deprotected using a TFA (trifluoroacetic acid) cleavage cocktail Reagent K containing aromatic cationic scavengers for 2 hr at room temperature. The crude peptide was filtered from the spent resin and subsequently isolated by precipitation into ice cold diethyl ether. The crude peptide was dissolved in 50% acetic acid and subsequently diluted into 3 L of H$_2$O containing 0.1 mM GSSG and 0.2 mM GSH. The pH of this peptide solution was adjusted to 8.0 with NH$_4$OH and allowed to slowly stir

TABLE 5 pH and Concentration of Formulations at 1, 3, 6 and 12 Months

| Sample ID | Incubation Temp | 1 Month | | 3 Months | | 6 Months | | 12 months | |
|---|---|---|---|---|---|---|---|---|---|
| | | pH | Conc | pH | Conc | pH | Conc | pH | Conc |
| 10P6N | 5° C. | 6.03 | 9.63 | 6.03 | 9.63 | 6.06 | 9.85 | 6.07 | 10.2 |
| 10P6N | −20° C. | 6.03 | 9.54 | 6.03 | 9.54 | 6.07 | 9.94 | 6.10 | 9.96 |
| 10P6N | −70° C. | 6.05 | 9.85 | 6.05 | 9.85 | 6.09 | 9.77 | 6.09 | 10.1 |
| 25P6N | 5° C. | 6.00 | 24.72 | 6.00 | 25.78 | 6.04 | 25.08 | 6.06 | 25.8 |
| 25P6N | −20° C. | 6.00 | 24.76 | 6.00 | 25.31 | 6.05 | 24.34 | 6.05 | 24.97 |
| 25P6N | −70° C. | 5.98 | 24.35 | 5.98 | 25.53 | 6.05 | 24.85 | 6.09 | 23.71 | overnight. ShK spontaneously folds to a major thermodynamically favored isomer which is the biologically active form of the peptide. The folded peptide was loaded onto a preparative RP-HPLC column and purified using a gradient of MeCN versus $H_2O$ containing 0.05% TFA. The fractions containing the desired peptide purity were pooled together and lyophilized. The final yield was 35 mg from a 0.2 mmol synthesis; based upon starting resin this represents a yield of 8%.

SPECT/CT scanning of radiolabeled ShK-221. ShK-221 (100 µg) was radiolabelled with 2 mCi 111 Indium chloride (GE Healthcare, Arlington Heights, Ill. USA) in a 300 µL reaction containing 50 mM sodium acetate, pH5.0 for 30 min at 95° C. The reaction was quenched by the addition of EDTA to a final concentration of 50 mM, and the radiolabeling efficiency was assessed by reverse-phase HPLC (Luna 5µ C18(2) 100 A 250×4.6 mm column, Phenomenex, Torrance, Calif. USA) on an Agilent 1100 system using an IN/US Systems Gamma RAM Model 4 radio-HPLC detector (LabLogic Systems, Brandon, Fla. USA). The labeling efficiency varied from 89-98% by this method. SPECT/CT scanning (NanoSPECT/CT Preclinical Imager, Mediso, Budapest, Hungary) was carried out on anesthetized animals in four 15 minute scans during the first hour and one scan each at 4, 8, 24, 48, 72, 120 and 160 hours post dose. The individual projection frame time for each helical SPECT was set such that the duration of each scan would last for approximately 15 to 45 minutes (varying by time-point to account for isotope decay) and allow for significant collection of statistics within each frame. The characteristic peaks detected from the spectra for 111In were 245 and 171 keV (primary and secondary, respectively). The resulting projection data were reconstructed after each scan using an iterative model that takes advantage of the pinhole geometry to achieve a resolution of approximately 2 mm.

Approximately 10 µL blood samples were collected after each scan and the amount of radioactivity in the sample was measured using a Wallac Wizard 1470 scintillation counter (Perkin Elmer, Waltham, Mass. USA). Drug concentrations were computed by taking account of the specific activity of the administered dose, the half-life of 111In (67.3 hours) and the counting efficiency of the instrument.

Statistical and computational analysis. Statistical analysis was carried out using the paired t-test. Goodness of model fit was determined using the $R^2$ statistic. Pharmacokinetic calculations were as follows: $C_{max}$ and $T_{max}$ were as observed in the dataset. AUC was computed using a linear trapezoidal method. The terminal elimination half-life was computed from the slope of the regression with the best adjusted $R^2$ value. $AUC_{t-\infty}$ was calculated by dividing the last observed drug concentration by the terminal elimination slope.

Figure 2A:
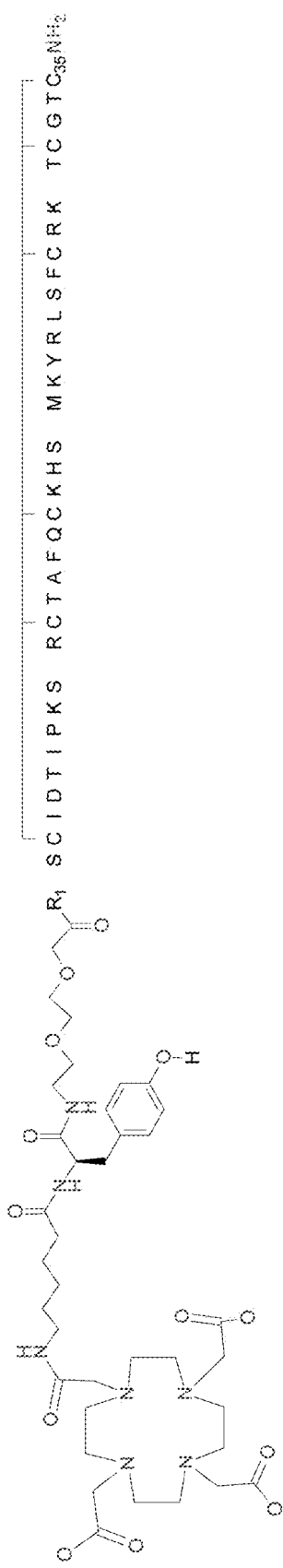
FIGS. 2A-2C illustrate the development of a radiolabeled analog of ShK-186. Radiolabeling of ShK-186 was carried out by solid-phase coupling of DOTA to the amino terminus of ShK-198 via a linker to form ShK-221 (SEQ ID NO:6.
Figure 2B:
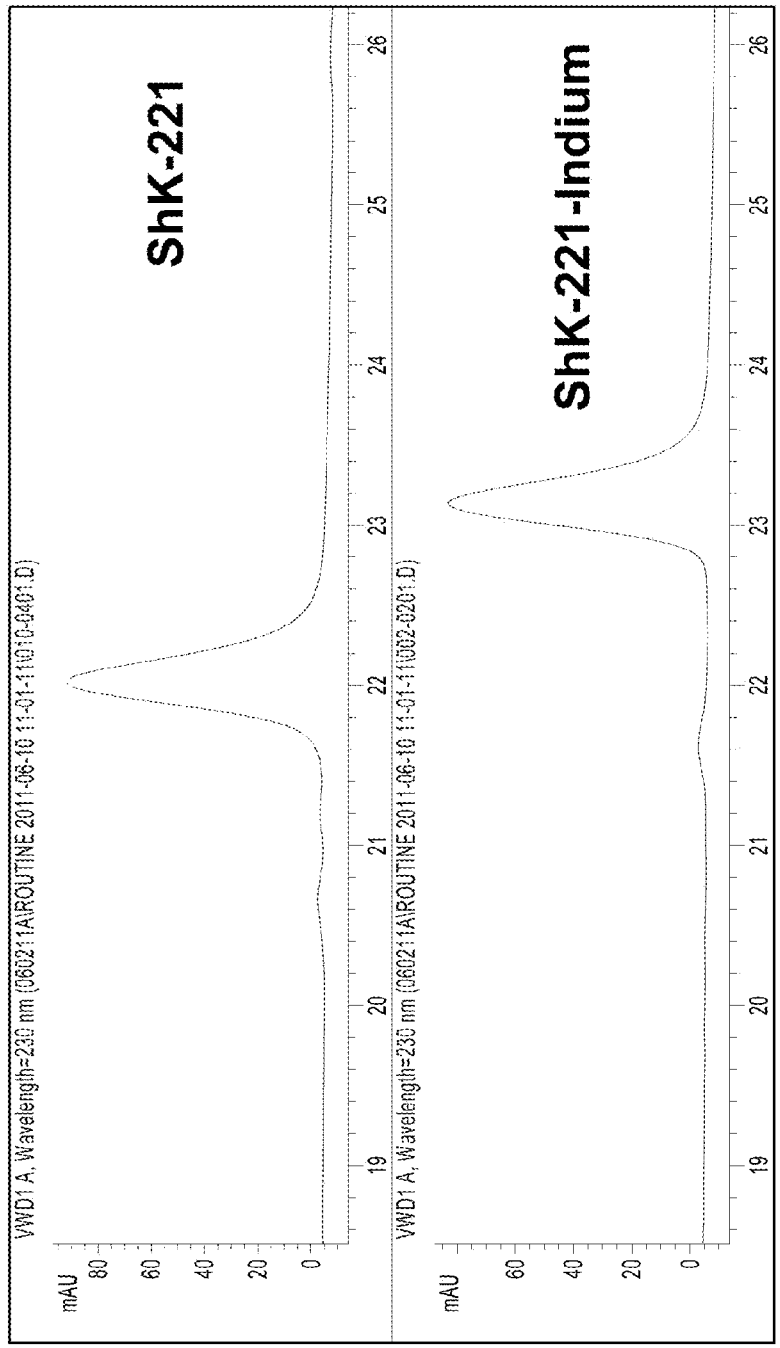
Figure 2C:
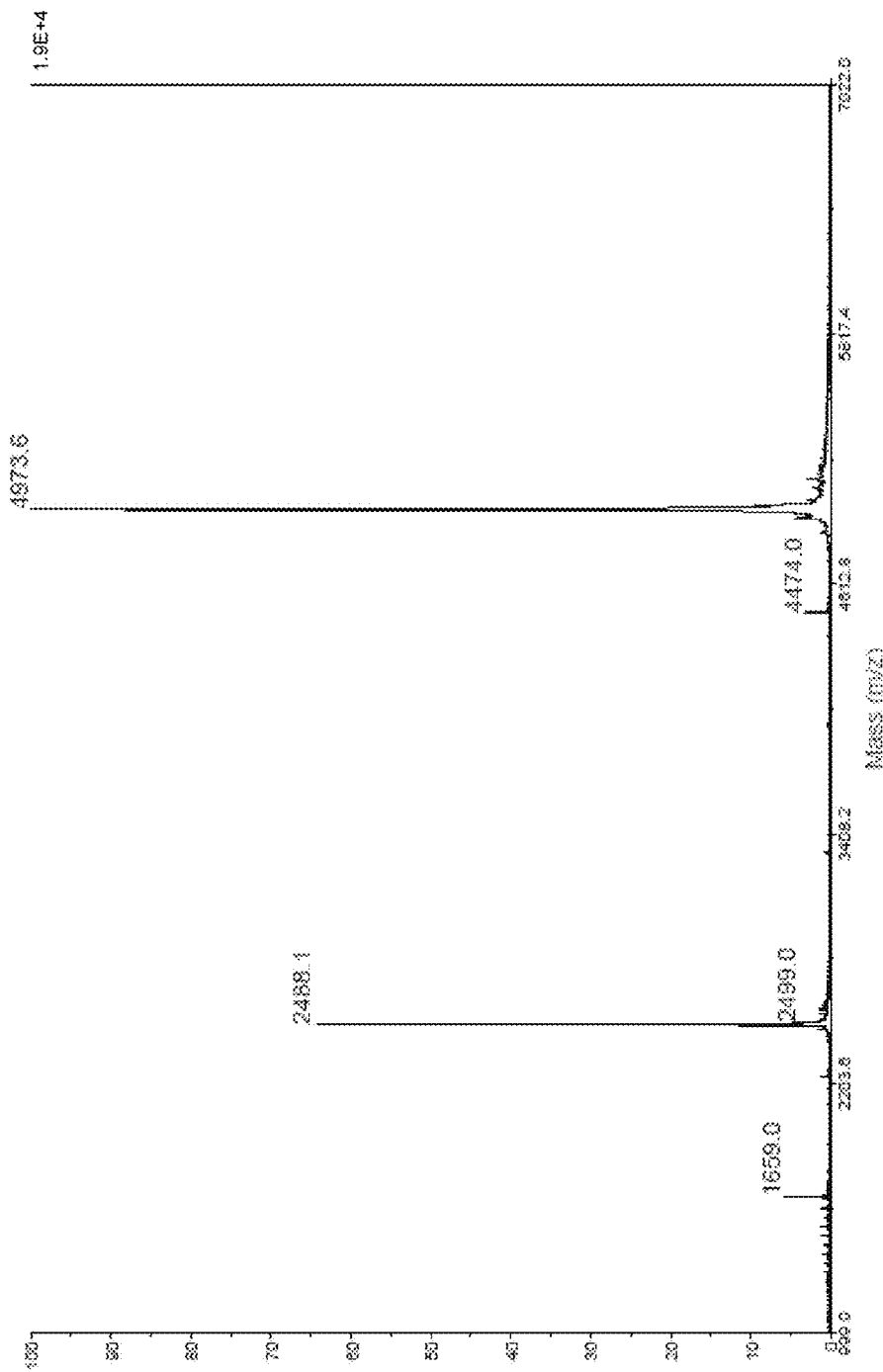
Figure 3A:
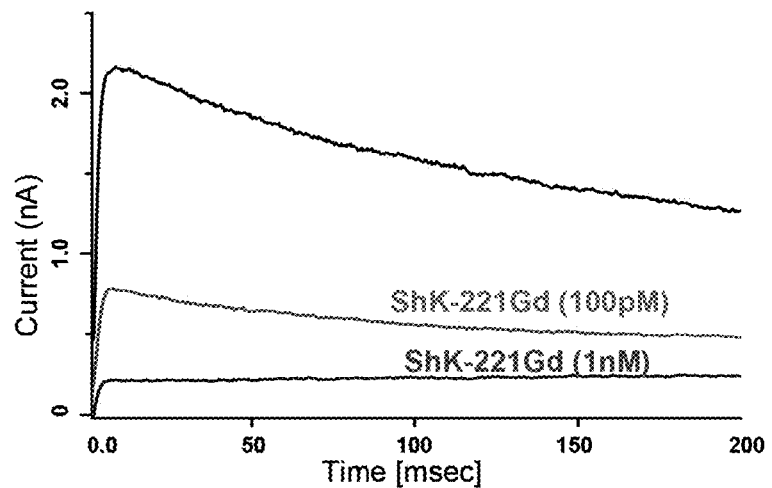
FIGS. 3A and 3B show a comparison of the Kv1.3 channel-blocking potency of ShK-186 and two labeled analogs, ShK-221-gadolinium (ShK-221-Gd) and ShK-221-indium (ShK-221-In)
Figure 3B:
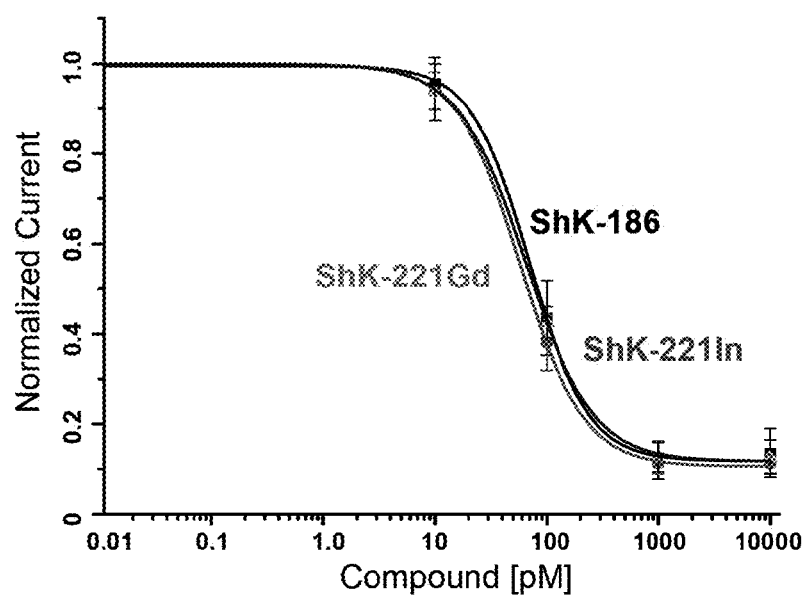

Results of ADME studies with a radiolabeled analog of ShK-186. ShK-186 contains a single iodinatable tyrosine at position 23. However, iodine incorporation into the ring, which is predicted to interact within the pore region of the Kv1.3 channel (Pennington et al., *Biochemistry* 35:16407-16411, 1996), results in disruption of the channel binding properties of the drug. The amino terminus of ShK-198 was therefore modified with a six-carbon linker attached via a peptide bond to one of the carboxylic acids of a DOTA chelate (FIG. 2A). The DOTA-conjugate, designated ShK-221, was readily coordinated with indium or gadolinium (FIGS. 2B-2C) and retained the full activity of the parent molecule (FIGS. 3A-3B). $^{111}$In-labeled ShK-221 was prepared and administered by subcutaneous injection to Sprague Dawley rat (1.0 mCi, 100 µg/kg) and squirrel monkey (0.83 mCi, 35 µg/kg). The radiolabeling efficiency ranged from 89-98% over the series of experiments as determined by HPLC. Biodistribution of radiolabeled ShK-221 was evaluated by SPECT imaging continuously for the first hour post-dose, and then at 4, 8, 24, 48, 72, 120, and 160 h. Background levels in the detection system were approximately 0.1 µCi/m³ (~5 ng/m³ of ShK-221 at the initial time point and 26 ng/m³ at the last time point). Blood samples were collected following each scan, and total radioactivity in whole blood was measured by scintillation counting. Computed tomography was performed at each time point to enable colocalization of the radiolabel with key anatomical structures.

Figures 1E, 1F:
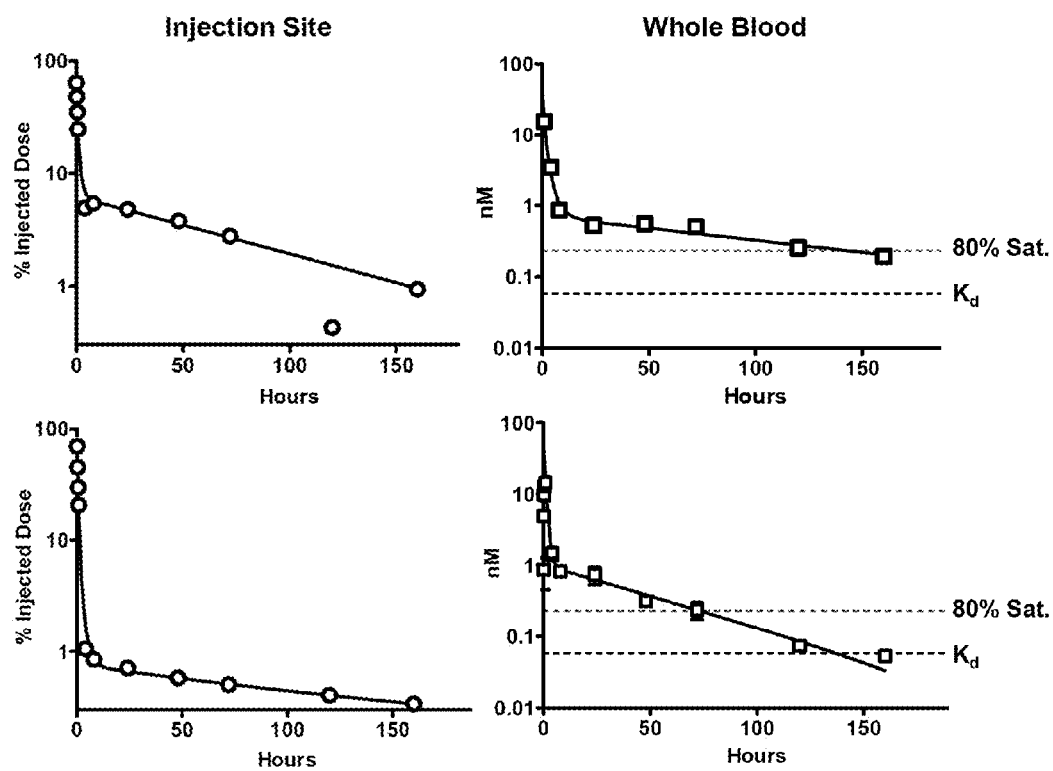

Biodistribution of $^{111}$In-ShK-221 in the squirrel monkey was characterized principally by slow absorption from the injection site over the entire 160 hour period (FIGS. 1A and 1E). The quantity of drug present at the injection site followed a biphasic exponential decay ($R^2$=0.95) with an initial half-life of approximately 1-1.5 hours and a terminal half-life of >48 hours (FIG. 1E). During the first hour, significant radioactivity could be observed in the kidney, increasing in intensity through 1 hour (~1% injected dose (ID)/g, Table 1) and slowly declining to approximately baseline by 48 hours. Radioactivity in the monkey kidney was primarily observed in the cortical and medullary regions during all time points and was comparatively absent in the renal pelvis except for the first hour (FIG. 1B). Significant bladder associated radioactivity ($T_{max}$=0.75-1 h, 0.34% ID/g) was only observed during the first four hours, after which relatively little radiolabel was detected in bladder. No other organ showed significant levels of radioactivity except for liver, which peaked at 0.75-1 hour post dose administration (0.166% ID/g). Muscle, heart and brain all had <0.1% ID/g at all time points (Table 6).

TABLE 6

Maximum concentration of $^{111}$In-ShK-221 in specific tissues of squirrel monkey following a 35 µg/kg subcutaneous injection

| Tissue | Maximum Scan Period (h) | Maximum (% injected dose/g) |
| --- | --- | --- |
| Injection Site | 0-0.25 | 17.3 |
| Kidneys | 0.75-1.0 | 0.976 |
| Bladder | 0.75-1.0 | 0.338 |
| Liver | 0.75-1.0 | 0.166 |
| Heart | 0.75-1.0 | 0.093 |
| Muscle | 0.5-0.75 | 0.039 |
| Brain | 0.75-1.0 | 0.020 |

Biodistribution of $^{111}$In-ShK-221 in the rat was similar to monkey and characterized by slightly faster absorption from the injection site and excretion through the urine over the first 24 hours (FIGS. 1C and 1E). Significant radioactive label was observed in rat bladder (9.4% ID/g), kidney (2.9% ID/g) and liver (0.4% ID/g) during the first hour (FIG. 1C). While little label was identified in the bladder at later time points, the amount of drug in liver and kidney was relatively constant through the first 24 h. Cross-sectional views of the rat kidney showed that, with the exception of the first hour, radioactivity was concentrated primarily in the cortical regions similar to the monkey (FIG. 1D).

Evaluation of blood-associated radioactivity in monkey at each time point also demonstrated a biphasic exponential decay ($R^2$=0.99) with an initial half-life of approximately 1 hour and a terminal half-life of >64 hours (FIG. 1F). In monkey, much of the terminal elimination phase was reflected by blood concentrations below the level of quantitation of previous methods but well above the $K_d$ for ShK-186. 80% of the Kv1.3 channels in whole blood would be expected to be bound by drug through approximately 5 days post-dose, and concentrations remain above the $K_d$ for the entire 160 hour period.

The whole blood-associated radioactivity in the rat also showed a biphasic exponential decay ($R^2$=0.99) with an initial half-life of approximately 1.7 hours and a terminal half-life of >72 hours (FIG. 1F). The drug concentrations, like the monkey, were well above the $K_d$ for ShK-186 until 5 days post dose. 80% of the Kv1.3 channels in whole blood would be expected to be bound by drug approximately 3-5 days post-dose.

The data show that biodistribution of radiolabeled ShK-221 in rat and squirrel monkey is characterized by a very slow distribution from the injection site, significant concentrations of drug peripherally in the injection site, kidney, and liver and a long terminal elimination phase in whole blood. Drug levels remained above ~200 pM in blood for approximately 7 days in the monkey and 3 days in the rat.

Significant amounts of radioactivity were observed in the bladder of both rat (~17% injected dose) and monkey (~1% injected dose) at the earliest time points following administration of 111In-ShK-221, suggesting that glomerular filtration is the principal elimination pathway for the peptide shortly after injection. The large amount of drug excreted by the rat in the first hour is most likely a reflection of the increased metabolism of the rat compared to the monkey. Following 1 hour in rat and approximately 4 hours in monkey, little radioactivity was observed in bladder whereas significant amounts of radioactivity were still observed in the kidney cortex. Cortical concentration has been reported for numerous radiolabeled versions of peptide drugs including octreotide, bombesin, exendin, and gastrin (Gotthardt et al., J. Nucl. Med. 48:596-601, 2007). The mechanism of cortical retention has been most thoroughly described for octreotide. Tubular reabsorption of the cationic octapeptide is mediated by megalin, a scavenger receptor expressed in the proximal kidney tubule (de Jong et al., J. Nucl. Med. 46:1696-1700, 2005). Mice with a kidney-specific disruption of the receptor lack the cortical retention of radiolabeled octreotide seen in wild-type mice. Renal uptake of octreotide is partially mediated by charge and can be disrupted by co-infusion of the positively charged amino acids L-lysine and L-arginine (Bodei et al., Eur. J. Nucl. Med. Mol. Imaging 30:207-216, 2003). ShK-186 carries a net +6 charge at physiological pH, and so its cortical retention may be mediated by a similar mechanism.

In summary, ADME studies with radiolabeled ShK suggest that a single dose of drug can provide therapeutically meaningful blood concentrations for up to 5 days in rat and 7 days in monkey. These observations are relevant to the clinical development of ShK-based peptide therapeutics, including ShK-186, since an optimized dose frequency will ensure therapeutic efficacy, improve patient compliance, and reduce the potential for drug accumulation during chronic administration.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods disclosed herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are disclosed herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically disclosed herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

What is claimed is:

1. A pharmaceutical composition comprising a pharmaceutically acceptable salt of an ShK polypeptide having the sequence of SEQ ID NO:5, wherein the C-terminus is an amide, and wherein the pH of the pharmaceutical composition is between 5 and 7 and the pharmaceutical composition further comprises a surfactant in an amount effective to dissolve the ShK polypeptide in an aqueous carrier.

2. The pharmaceutical composition of claim 1 wherein the pharmaceutical composition is contained in a sterile glass vial and is stored at −70° C.

3. The pharmaceutical composition of claim 1 formulated for subcutaneous administration.

4. The pharmaceutical composition of claim 1 wherein the pharmaceutical composition is contained in a sterile syringe.

5. A unit of manufacture for pharmaceutical use comprising:
a pharmaceutical composition comprising a pharmaceutically acceptable salt of an ShK polypeptide having the sequence of SEQ ID NO:5, wherein the C-terminus is an amide and instructions for diluting and preparing the pharmaceutical composition for administration to a human, wherein the pH of the pharmaceutical composition is between 5 and 7 and the pharmaceutical composition further comprises a surfactant in an amount effective to dissolve the ShK polypeptide in an aqueous carrier, and wherein the pharmaceutical composition is contained in at least one glass vial prepared under sterile conditions such that the pharmaceutical composition within the at least one glass vial is stable for at least six months at −70° C.

6. A unit of manufacture for pharmaceutical use comprising:
a pharmaceutical composition comprising a pharmaceutically acceptable salt of an ShK polypeptide having the sequence of SEQ ID NO:5, wherein the C-terminus is an amide and instructions for administering the pharmaceutical composition to a human, wherein the pH of the pharmaceutical composition is between 5 and 7 and the pharmaceutical composition further comprises a surfactant in an amount effective to dissolve the ShK polypeptide in an aqueous carrier, and wherein the pharmaceutical composition is contained in at least one sterile syringe.

* * * * *